United States Patent
Osswald et al.

(10) Patent No.: US 7,943,359 B2
(45) Date of Patent: May 17, 2011

(54) POLYNUCLEOTIDES WHICH CODE FOR CYANIDE-TOLERANT NITRILE HYDRATASE AND COMPOSITIONS THEREOF

(75) Inventors: Steffen Osswald, Rodenbach (DE);
Christoph Weckbecker, Gründau (DE);
Klaus Huthmacher, Gelnhausen (DE);
Tatijana Gerasimova, Moscow (RU);
Andrey Novikov, Moscow (RU);
Ludmila Ryabchenko, Odintcovo (RU);
Alexander Yanenko, Moscow (RU);
Ksenia Egorova, Hamburg (DE)

(73) Assignee: Evonik Degussa GmbH, Essen (DE)

( * ) Notice: Subject to any disclaimer, the term of this patent is extended or adjusted under 35 U.S.C. 154(b) by 0 days.

(21) Appl. No.: 12/539,804

(22) Filed: Aug. 12, 2009

(65) Prior Publication Data
US 2010/0261250 A1    Oct. 14, 2010

Related U.S. Application Data

(62) Division of application No. 10/598,873, filed as application No. PCT/EP2005/002689 on Mar. 14, 2005, now Pat. No. 7,592,165.

(30) Foreign Application Priority Data
Mar. 20, 2004   (DE) .................. 10 2004 013 847

(51) Int. Cl.
C12P 13/02   (2006.01)
C12N 9/00   (2006.01)
C12N 9/14   (2006.01)
C12N 1/20   (2006.01)
C07H 21/04   (2006.01)

(52) U.S. Cl. ..... 435/195; 435/129; 435/183; 435/252.3; 536/23.2

(58) Field of Classification Search .................. None
See application file for complete search history.

(56) References Cited

OTHER PUBLICATIONS

Chica et al. Curr Opin Biotechnol. Aug. 2005;16(4):378-84.*
Sen et al. Appl Biochem Biotechnol. Dec. 2007;143(3):212-23.*
Accession AAQ13362. Nov. 13, 1991.*
Beppu et al. Accession AAR13831, Nov. 13, 1991.
International Search Report and Written Opinion mailed Nov. 9, 2006 in PCT/EP2005-002689.

* cited by examiner

*Primary Examiner* — Christian L Fronda
(74) *Attorney, Agent, or Firm* — Smith, Gambrell & Russell, LLP

(57) ABSTRACT

Disclosed herein are cyanide-tolerant nitrile hydratases especially from *Pseudomonas putida* or *Pseudomonas marginalis* strains which exhibit increased cyanide tolerance. Also disclosed are methods of preparing amides from nitriles in the presence of cyanides and polynucleotide sequences coding for cyanide-tolerant nitrile hydratases.

6 Claims, 7 Drawing Sheets

MA32

MA113

MA31

MA113

MA113

MA32

```
                          SEQUENCE LISTING

<160> NUMBER OF SEQ ID NOS: 14

<210> SEQ ID NO 1
<211> LENGTH: 6828
<212> TYPE: DNA
<213> ORGANISM: Pseudomonas marginalis
<220> FEATURE:
<221> NAME/KEY: CDS
<222> LOCATION: (25)..(609)
<223> OTHER INFORMATION: Coding region of alpha-subunit gene
<220> FEATURE:
<221> NAME/KEY: CDS
<222> LOCATION: (650)..(1312)
<223> OTHER INFORMATION: Coding region of beta-subunit gene
<220> FEATURE:
<221> NAME/KEY: gene
<222> LOCATION: (1309)..(2577)
<223> OTHER INFORMATION: Gene of activator protein

<400> SEQUENCE: 1
aattcttaag aaggagatat acat atg agt aca gct act tca acg ccc ggc           51
                            Met Ser Thr Ala Thr Ser Thr Pro Gly
                              1               5 gaa aga gcc tgg gca ttg ttt caa gtc ctc aag agc aag gaa ctc atc          99
Glu Arg Ala Trp Ala Leu Phe Gln Val Leu Lys Ser Lys Glu Leu Ile
 10              15                  20                  25 ccg gag ggc tat gtc gag cag ctc acg caa ttg atg gag cac ggc tgg         147
Pro Glu Gly Tyr Val Glu Gln Leu Thr Gln Leu Met Glu His Gly Trp
             30                  35                  40 agc ccc gag aac ggc gcc cgt gtg gtg gcc aag gcg tgg gtc gat ccg         195
Ser Pro Glu Asn Gly Ala Arg Val Val Ala Lys Ala Trp Val Asp Pro
         45                  50                  55 cag ttc cgg gca ctg ttg ctc aag gac ggc acc gcg gcc tgc gcc cag         243
Gln Phe Arg Ala Leu Leu Leu Lys Asp Gly Thr Ala Ala Cys Ala Gln
     60                  65                  70 ttc ggc tac acc ggc ccc cag ggc gaa tac atc gtt gcc ctg gag gat         291
Phe Gly Tyr Thr Gly Pro Gln Gly Glu Tyr Ile Val Ala Leu Glu Asp
 75                  80                  85 acg ccg acg ctg aag aac gtg att gtc tgc agc ctg tgc tcc tgc acc         339
Thr Pro Thr Leu Lys Asn Val Ile Val Cys Ser Leu Cys Ser Cys Thr
 90                  95                 100                 105 aac tgg ccg gtc ctc ggc ctg cca ccg gag tgg tac aag ggt ttc gag         387
Asn Trp Pro Val Leu Gly Leu Pro Pro Glu Trp Tyr Lys Gly Phe Glu
             110                 115                 120 ttc cgc gca cgc ctg gtc cgg gag ggg cgc acg gta ctg cgc gag ctg         435
Phe Arg Ala Arg Leu Val Arg Glu Gly Arg Thr Val Leu Arg Glu Leu
         125                 130                 135 ggg acg gag ttg ccc cgg gac atg gtg gtc aag gtc tgg gac acc agc         483
Gly Thr Glu Leu Pro Arg Asp Met Val Val Lys Val Trp Asp Thr Ser
     140                 145                 150 gcc gaa agc cgc tac ctg gtg ctg ccg gtc agg ccg gaa ggc tca gaa         531
```

```
Ala Glu Ser Arg Tyr Leu Val Leu Pro Val Arg Pro Glu Gly Ser Glu
            155                 160                 165 cac atg agc gaa gag cag ctt caa gcg ctg gtg acc aaa gac gtg ctg         579
His Met Ser Glu Glu Gln Leu Gln Ala Leu Val Thr Lys Asp Val Leu
170                 175                 180                 185 atc ggc gtc gcc ctg ccc cgc gtg ggc tga gaacaacacc tcatcatcgt           629
Ile Gly Val Ala Leu Pro Arg Val Gly
                        190 tcactcccgg agttttgatt atg gat ggc ttt cac gat ctc ggc ggt ttc caa       682
                      Met Asp Gly Phe His Asp Leu Gly Gly Phe Gln
                      195                 200                 205 ggc ttt gga aaa gtc cct cac acc atc aac agc ctg agc tac aaa cag         730
Gly Phe Gly Lys Val Pro His Thr Ile Asn Ser Leu Ser Tyr Lys Gln
                    210                 215                 220 gtg ttc aag cag gac tgg gag cat ctg gcc tac agc ttg atg ttc atc         778
Val Phe Lys Gln Asp Trp Glu His Leu Ala Tyr Ser Leu Met Phe Ile
                225                 230                 235 ggt gcc gac cac ttg aaa aag ttc agc gtg gac gaa gtg cgt cac gcc         826
Gly Ala Asp His Leu Lys Lys Phe Ser Val Asp Glu Val Arg His Ala
            240                 245                 250 gtc gaa cgc ctg gat gtg cgc cag cat gtc ggc acc cag tac tac gaa         874
Val Glu Arg Leu Asp Val Arg Gln His Val Gly Thr Gln Tyr Tyr Glu
255                 260                 265 cgc tac gtc atc gcg acc gcc acc ctg ctg gtc gaa acc ggc gtg atc         922
Arg Tyr Val Ile Ala Thr Ala Thr Leu Leu Val Glu Thr Gly Val Ile
270                 275                 280                 285 acc cag gcg gag ctt gat cag gcc ttg ggc tcc cac ttc aag ctg gcg         970
Thr Gln Ala Glu Leu Asp Gln Ala Leu Gly Ser His Phe Lys Leu Ala
                290                 295                 300 aat ccc gcc cat gcc gag ggc cgc ccg gcg att acg ggg cgg ccg ccc        1018
Asn Pro Ala His Ala Glu Gly Arg Pro Ala Ile Thr Gly Arg Pro Pro
            305                 310                 315 ttc gag gtg ggg gat cgg gtg gtg gtg cga gac gaa tat gtg gct gga        1066
Phe Glu Val Gly Asp Arg Val Val Val Arg Asp Glu Tyr Val Ala Gly
        320                 325                 330 cac atc cgc atg ccc gcc tac gtg cgc ggc aag gaa ggc gtg gtc ctg        1114
His Ile Arg Met Pro Ala Tyr Val Arg Gly Lys Glu Gly Val Val Leu
335                 340                 345 cac cgc acg tca gag aaa tgg ccg ttc ccc gac gca atc ggg cat ggc        1162
His Arg Thr Ser Glu Lys Trp Pro Phe Pro Asp Ala Ile Gly His Gly
350                 355                 360                 365 gat gta agc gca gcc cat caa ccc acc tac cac gtc gag ttc gcc gtg        1210
Asp Val Ser Ala Ala His Gln Pro Thr Tyr His Val Glu Phe Ala Val
                370                 375                 380 aag gac ctg tgg gga gat gcc gcc gat gag ggt ttt gtg gtg gtc gac        1258
Lys Asp Leu Trp Gly Asp Ala Ala Asp Glu Gly Phe Val Val Val Asp
            385                 390                 395 ctg ttc gaa agc tac ctg gac aag gcc gcc ggc gcg cgc gcg gtg aac        1306
Leu Phe Glu Ser Tyr Leu Asp Lys Ala Ala Gly Ala Arg Ala Val Asn
        400                 405                 410 cca tga cagacggcgc ccaggcaagc cgactgccgg tgacggtcct ttcgggcttc         1362
Pro
ctcggcgccg gcaagaccac cctgctcaac cacatcctgc gcaatcgcga aggcctgcgc      1422
gtggccgtca tcgtcaatga catgagcgaa gtcaatatcg atgccgaaga ggtgcagcgc      1482
gatgtcgcgc tgcaccgtgg tcgcgatgag ctgatcgaga tgagcaacgg tgcatctgc       1542 tgcaccctgc gcgccgattt gctcgagcag atcagcatgc tcgcacgcca acagcgtttc      1602
gattacctgc tgattgaatc cacggggatc tccgagccga tgccggtcgc ggagacgttc      1662
gccttccttg acgctgatgg cttcagcctc agcgaactgg cgcgcctgga caccttggtg      1722
```

```
acggtggtcg atggcagtcg tttccaggaa ctgctcgaat cgccgcacac cgttgaccag   1782
gatgacgcca cgccagacgc acccaagcgc cacctggccg atctgctgat cgaacaggtg   1842
gagtacgcca acgtcattct cgtcaataag ctggatctga tcgatgcagc gcagtatcag   1902
gccgtgcagg cgatcctcac aggccttaac ccgacggcgc ggatcatgcc gatggcccac   1962
ggtaacatcc catcagccag cctgctcggc acccatctgt ttgatttacc cagcctcgcg   2022
gcgtcgccgg gctggatgcg gaaaatggag gcggcagacg cgccggcctc cgagtcggac   2082
acctatggcg tgacgtcctg ggtgtaccgt gagcgcgcac cttccaccc gcaacgttg    2142 ctcgactttc tccagcagcc ctggtgcaac gggcggttgc tgcgcagcaa aggttacttc   2202
tggcttgcca gccgccacct ggaaaccggc ctgctggtgc aaagcggcaa gcggttccag   2262
tgggactatg tcgggcgctg gtggaacttc atcgagccgt cgcaatggcc ccgggacgaa   2322
taccggctgc agggcatcag ggccaaatgg gacagcgtgg tcggcgactg ccggcaggag   2382
ttggtgttta tcgccagggg cctcgacacc gacgcgttac agcgcgagct cgaccactgc   2442
ctgctgagcg cccaggaaat cgccgccggc ccactggcct ggcaagcgct gccggggcg    2502 accgcctttg accgacagac ccttgcccgc cccccacaca gcccatggcg attgccccca   2562
tttgatccga gatagaagct tctgttttgg cggatgagag aagattttca gcctgataca   2622
gattaaatca gaacgcagaa gcggtctgat aaaacagaat ttgcctggcg gcagtagcgc   2682
ggtggtccca cctgaccccca tgccgaactc agaagtgaaa cgccgtagcg ccgatggtag   2742 tgtgggtct ccccatgcga gagtagggaa ctgccaggca tcaaataaaa cgaaaggctc    2802
agtcgaaaga ctgggccttt cgttttatct gttgtttgtc ggtgaacgct ctcctgagta   2862
ggacaaatcc gccgggagcg gatttgaacg ttgcgaagca acggcccgga gggtggcggg   2922
caggacgccc gccataaact gccaggcatc aaattaagca gaaggccatc ctgacggatg   2982
gcctttttgc gtttctacaa actctttgt ttattttct aaatacattc aaatatgtat      3042
ccgctcatga gacaataacc ctgataaatg cttcaataat attgaaaaag gaagagtatg   3102
agtattcaac atttccgtgt cgcccttatt cccttttttg cggcattttg ccttcctgtt   3162
tttgctcacc cagaaacgct ggtgaaagta aaagatgctg aagatcagtt gggtgcacga   3222
gtgggttaca tcgaactgga tctcaacagc ggtaagatcc ttgagagttt tcgccccgaa   3282
gaacgttttc caatgatgag cacttttaaa gttctgctat gtggcgcggt attatcccgt   3342
gttgacgccg gcaagagcaa actcggtcgc cgcatacact attctcagaa tgacttggtt   3402
gagtactcac cagtcacaga aaagcatctt acggatggca tgacagtaag agaattatgc   3462
agtgctgcca taaccatgag tgataacact gcggccaact tacttctgac aacgatcgga   3522
ggaccgaagg agctaaccgc ttttttgcac aacatggggg atcatgtaac tcgccttgat   3582
cgttgggaac cggagctgaa tgaagccata ccaaacgacg agcgtgacac cacgatgcct   3642
gtagcaatgg caacaacgtt gcgcaaacta ttaactggcg aactacttac tctagcttcc   3702
cggcaacaat taatagactg gatggaggcg gataaagttg caggaccact tctgcgctcg   3762
gcccttccgg ctggctggtt tattgctgat aaatctggag ccggtgagcg tgggtctcgc   3822
ggtatcattg cagcactggg gccagatggt aagccctccc gtatcgtagt tatctacacg   3882
acggggagtc aggcaactat ggatgaacga atagacaga tcgctgagat aggtgcctca    3942
ctgattaagc attggtaact gtcagaccaa gtttactcat atatacttta gattgattta   4002
aaacttcatt tttaatttaa aaggatctag gtgaagatcc ttttttgataa tctcatgacc   4062 aaaatccctt aacgtgagtt ttcgttccac tgagcgtcag accccgtaga aaagatcaaa   4122
```

-continued

```
ggatcttctt gagatccttt ttttctgcgc gtaatctgct gcttgcaaac aaaaaaacca   4182
ccgctaccag cggtggtttg tttgccggat caagagctac caactcttt tccgaaggta   4242
actggcttca gcagagcgca gataccaaat actgtccttc tagtgtagcc gtagttaggc   4302
caccacttca agaactctgt agcaccgcct acatacctcg ctctgctaat cctgttacca   4362
gtggctgctg ccagtggcga taagtcgtgt cttaccgggt tggactcaag acgatagtta   4422
ccggataagg cgcagcggtc gggctgaacg gggggttcgt gcacacagcc cagcttggag   4482
cgaacgacct acaccgaact gagataccta cagcgtgagc tatgagaaag cgccacgctt   4542
cccgaaggga gaaggcgga caggtatccg gtaagcggca gggtcggaac aggagagcgc   4602
acgagggagc ttccaggggg aaacgcctgg tatctttata gtcctgtcgg gtttcgccac   4662
ctctgacttg agcgtcgatt tttgtgatgc tcgtcagggg ggcggagcct atggaaaaac   4722
gccagcaacg cggccttttt acggttcctg gccttttgct ggccttttgc tcacatgttc   4782
tttcctgcgt tatcccctga ttctgtggat aaccgtatta ccgcctttga gtgagctgat   4842
accgctcgcc gcagccgaac gaccgagcgc agcgagtcag tgagcgagga agcggaagag   4902
cgcctgatgc ggtattttct ccttacgcat ctgtgcggta tttcacaccg catatatggt   4962
gcactctcag tacaatctgc tctgatgccg catagttaag ccagtataca ctccgctatc   5022
gctacgtgac tgggtcatgg ctgcgccccg acacccgcca cacccgctg acgcgcctg   5082
acgggcttgt ctgctcccgg catccgctta cagacaagct gtgaccgtct ccgggagctg   5142
catgtgtcag aggttttcac cgtcatcacc gaaacgcgcg aggcagctgc ggtaaagctc   5202
atcagcgtgg tcgtgaagcg attcacagat gtctgcctgt tcatccgcgt ccagctcgtt   5262
gagtttctcc agaagcgtta atgtctggct tctgataaag cgggccatgt taagggcggt   5322
tttttcctgt ttggtcactt gatgcctccg tgtaaggggg aatttctgtt catgggggta   5382
atgataccga tgaaacgaga gaggatgctc acgatacggg ttactgatga tgaacatgcc   5442
cggttactgg aacgttgtga gggtaaacaa ctggcggtat ggatgcggcg ggaccagaga   5502
aaaatcactc agggtcaatg ccagcgcttc gttaatacag atgtaggtgt tccacagggt   5562
agccagcagc atcctgcgat gcagatccgg aacataatgg tgcagggcgc tgacttccgc   5622
gtttccagac tttacgaaac acggaaaccg aagaccattc atgttgttgc tcaggtcgca   5682
gacgttttgc agcagcagtc gcttcacgtt cgctcgcgta tcggtgattc attctgctaa   5742
ccagtaaggc aaccccgcca gcctagccgg gtcctcaacg acaggagcac gatcatgcgc   5802
acccgtggcc aggacccaac gctgcccgag atgcgccgcg tgcggctgct ggagatggcg   5862
gacgcgatgg atatgttctg ccaagggttg gtttgcgcat tcacagttct ccgcaagaat   5922
tgattggctc caattcttgg agtggtgaat ccgttagcga ggtgccgccg gcttccattc   5982
aggtcgaggt ggcccggctc catgcaccgc gacgcaacgc ggggaggcag acaaggtata   6042
gggcggcgcg cctacaatcc atgccaaccc gttccatgtg ctcgccgagg cggcataaat   6102
cgccgtgacg atcagcggtc cagtgatcga agttaggctg gtaagagccg cgagcgatcc   6162
ttgaagctgt ccctgatggt cgtcatctac ctgcctggac agcatggcct gcaacgcggg   6222
catcccgatg ccgccggaag cgagaagaat cataatgggg aaggccatcc agcctcgcgt   6282
cgcgaacgcc agcaagacgt agcccagcgc gtcggccgcc atgccggcga taatggcctg   6342
cttctcgccg aaacgtttgg tggcgggacc agtgacgaag gcttgagcga gggcgtgcaa   6402
gattccgaat accgcaagcg acaggccgat catcgtcgcg ctccagcgaa agcggtcctc   6462
gccgaaaatg acccagagcg ctgccggcac ctgtcctacg agttgcatga taaagaagac   6522
```

-continued

```
agtcataagt gcggcgacga tagtcatgcc ccgcgcccac cggaaggagc tgactgggtt    6582
gaaggctctc aagggcatcg gtcgacgctc tcccttatgc gactcctgca ttaggaagca    6642
gcccagtagt aggttgaggc cgttgagcac cgccgccgca aggaatggtg catgcatcga    6702
tcaccacaat tcagcaaatt gtgaacatca tcacgttcat ctttccctgg ttgccaatgg    6762
cccattttcc tgtcagtaac gagaaggtcg cgaattcagg cgcttttttag actggtcgta    6822 atgaac                                                              6828
```

<210> SEQ ID NO 2
<211> LENGTH: 194
<212> TYPE: PRT
<213> ORGANISM: Pseudomonas marginalis

<400> SEQUENCE: 2

Met Ser Thr Ala Thr Ser Thr Pro Gly Glu Arg Ala Trp Ala Leu Phe
1               5                   10                  15

Gln Val Leu Lys Ser Lys Glu Leu Ile Pro Glu Gly Tyr Val Glu Gln
            20                  25                  30

Leu Thr Gln Leu Met Glu His Gly Trp Ser Pro Glu Asn Gly Ala Arg
        35                  40                  45

Val Val Ala Lys Ala Trp Val Asp Pro Gln Phe Arg Ala Leu Leu Leu
    50                  55                  60

Lys Asp Gly Thr Ala Ala Cys Ala Gln Phe Gly Tyr Thr Gly Pro Gln
65                  70                  75                  80

Gly Glu Tyr Ile Val Ala Leu Glu Asp Thr Pro Thr Leu Lys Asn Val
                85                  90                  95

Ile Val Cys Ser Leu Cys Ser Cys Thr Asn Trp Pro Val Leu Gly Leu
            100                 105                 110

Pro Pro Glu Trp Tyr Lys Gly Phe Glu Phe Arg Ala Arg Leu Val Arg
        115                 120                 125

Glu Gly Arg Thr Val Leu Arg Glu Leu Gly Thr Glu Leu Pro Arg Asp
    130                 135                 140

Met Val Val Lys Val Trp Asp Thr Ser Ala Glu Ser Arg Tyr Leu Val
145                 150                 155                 160

Leu Pro Val Arg Pro Glu Gly Ser Glu His Met Ser Glu Gln Leu
                165                 170                 175

Gln Ala Leu Val Thr Lys Asp Val Leu Ile Gly Val Ala Leu Pro Arg
            180                 185                 190

Val Gly

<210> SEQ ID NO 3
<211> LENGTH: 220
<212> TYPE: PRT
<213> ORGANISM: Pseudomonas marginalis

<400> SEQUENCE: 3

Met Asp Gly Phe His Asp Leu Gly Gly Phe Gln Gly Phe Gly Lys Val
1               5                   10                  15

Pro His Thr Ile Asn Ser Leu Ser Tyr Lys Gln Val Phe Lys Gln Asp
            20                  25                  30

Trp Glu His Leu Ala Tyr Ser Leu Met Phe Ile Gly Ala Asp His Leu
        35                  40                  45

Lys Lys Phe Ser Val Asp Glu Val Arg His Ala Val Glu Arg Leu Asp
    50                  55                  60

Val Arg Gln His Val Gly Thr Gln Tyr Tyr Glu Arg Tyr Val Ile Ala

```
                65                  70                  75                  80
Thr Ala Thr Leu Leu Val Glu Thr Gly Val Ile Thr Gln Ala Glu Leu
                    85                  90                  95

Asp Gln Ala Leu Gly Ser His Phe Lys Leu Ala Asn Pro Ala His Ala
                100                 105                 110

Glu Gly Arg Pro Ala Ile Thr Gly Arg Pro Pro Phe Glu Val Gly Asp
                115                 120                 125

Arg Val Val Arg Asp Glu Tyr Val Ala Gly His Ile Arg Met Pro
            130                 135                 140

Ala Tyr Val Arg Gly Lys Glu Gly Val Val Leu His Arg Thr Ser Glu
145                 150                 155                 160

Lys Trp Pro Phe Pro Asp Ala Ile Gly His Gly Asp Val Ser Ala Ala
                165                 170                 175

His Gln Pro Thr Tyr His Val Glu Phe Ala Val Lys Asp Leu Trp Gly
                180                 185                 190

Asp Ala Ala Asp Glu Gly Phe Val Val Val Asp Leu Phe Glu Ser Tyr
                195                 200                 205

Leu Asp Lys Ala Ala Gly Ala Arg Ala Val Asn Pro
            210                 215                 220

<210> SEQ ID NO 4
<211> LENGTH: 1269
<212> TYPE: DNA
<213> ORGANISM: Pseudomonas marginalis
<220> FEATURE:
<221> NAME/KEY: CDS
<222> LOCATION: (1)..(1269)
<223> OTHER INFORMATION: Coding region of activator protein gene

<400> SEQUENCE: 4 atg aca gac ggc gcc cag gca agc cga ctg ccg gtg acg gtc ctt tcg      48
Met Thr Asp Gly Ala Gln Ala Ser Arg Leu Pro Val Thr Val Leu Ser
1               5                   10                  15 ggc ttc ctc ggc gcc ggc aag acc acc ctg ctc aac cac atc ctg cgc      96
Gly Phe Leu Gly Ala Gly Lys Thr Thr Leu Leu Asn His Ile Leu Arg
            20                  25                  30 aat cgc gaa ggc ctg cgc gtg gcc gtc atc gtc aat gac atg agc gaa     144
Asn Arg Glu Gly Leu Arg Val Ala Val Ile Val Asn Asp Met Ser Glu
        35                  40                  45 gtc aat atc gat gcc gaa gag gtg cag cgc gat gtc gcg ctg cac cgt     192
Val Asn Ile Asp Ala Glu Glu Val Gln Arg Asp Val Ala Leu His Arg
    50                  55                  60 ggt cgc gat gag ctg atc gag atg agc aac ggg tgc atc tgc tgc acc     240
Gly Arg Asp Glu Leu Ile Glu Met Ser Asn Gly Cys Ile Cys Cys Thr
65                  70                  75                  80 ctg cgc gcc gat ttg ctc gag cag atc agc atg ctc gca cgc caa cag     288
Leu Arg Ala Asp Leu Leu Glu Gln Ile Ser Met Leu Ala Arg Gln Gln
                85                  90                  95 cgt ttc gat tac ctg ctg att gaa tcc acg ggg atc tcc gag ccg atg     336
Arg Phe Asp Tyr Leu Leu Ile Glu Ser Thr Gly Ile Ser Glu Pro Met
            100                 105                 110 ccg gtc gcg gag acg ttc gcc ttc ctt gac gct gat ggc ttc agc ctc     384
Pro Val Ala Glu Thr Phe Ala Phe Leu Asp Ala Asp Gly Phe Ser Leu
        115                 120                 125 agc gaa ctg gcg cgc ctg gac acc ttg gtg acg gtg gtc gat ggc agt     432
Ser Glu Leu Ala Arg Leu Asp Thr Leu Val Thr Val Val Asp Gly Ser
    130                 135                 140 cgt ttc cag gaa ctg ctc gaa tcg ccg cac acc gtt gac cag gat gac     480
Arg Phe Gln Glu Leu Leu Glu Ser Pro His Thr Val Asp Gln Asp Asp
145                 150                 155                 160
```

```
gcc acg cca gac gca ccc aag cgc cac ctg gcc gat ctg ctg atc gaa    528
Ala Thr Pro Asp Ala Pro Lys Arg His Leu Ala Asp Leu Leu Ile Glu
            165                 170                 175 cag gtg gag tac gcc aac gtc att ctc gtc aat aag ctg gat ctg atc    576
Gln Val Glu Tyr Ala Asn Val Ile Leu Val Asn Lys Leu Asp Leu Ile
        180                 185                 190 gat gca gcg cag tat cag gcc gtg cag gcg atc ctc aca ggc ctt aac    624
Asp Ala Ala Gln Tyr Gln Ala Val Gln Ala Ile Leu Thr Gly Leu Asn
                195                 200                 205 ccg acg gcg cgg atc atg ccg atg gcc cac ggt aac atc cca tca gcc    672
Pro Thr Ala Arg Ile Met Pro Met Ala His Gly Asn Ile Pro Ser Ala
        210                 215                 220 agc ctg ctc ggc acc cat ctg ttt gat tta ccc agc ctc gcg gcg tcg    720
Ser Leu Leu Gly Thr His Leu Phe Asp Leu Pro Ser Leu Ala Ala Ser
225                 230                 235                 240 ccg ggc tgg atg cgg aaa atg gag gcg gca gac gcg ccg gcc tcc gag    768
Pro Gly Trp Met Arg Lys Met Glu Ala Ala Asp Ala Pro Ala Ser Glu
                245                 250                 255 tcg gac acc tat ggc gtg acg tcc tgg gtg tac cgt gag cgc gca cct    816
Ser Asp Thr Tyr Gly Val Thr Ser Trp Val Tyr Arg Glu Arg Ala Pro
            260                 265                 270 ttc cac ccg caa cgg ttg ctc gac ttt ctc cag cag ccc tgg tgc aac    864
Phe His Pro Gln Arg Leu Leu Asp Phe Leu Gln Gln Pro Trp Cys Asn
        275                 280                 285 ggg cgg ttg ctg cgc agc aaa ggt tac ttc tgg ctt gcc agc cgc cac    912
Gly Arg Leu Leu Arg Ser Lys Gly Tyr Phe Trp Leu Ala Ser Arg His
    290                 295                 300 ctg gaa acc ggc ctg ctg gtg caa agc ggc aag cgg ttc cag tgg gac    960
Leu Glu Thr Gly Leu Leu Val Gln Ser Gly Lys Arg Phe Gln Trp Asp
305                 310                 315                 320 tat gtc ggg cgc tgg tgg aac ttc atc gag ccg tcg caa tgg ccc cgg    1008
Tyr Val Gly Arg Trp Trp Asn Phe Ile Glu Pro Ser Gln Trp Pro Arg
                325                 330                 335 gac gaa tac cgg ctg cag ggc atc agg gcc aaa tgg gac agc gtg gtc    1056
Asp Glu Tyr Arg Leu Gln Gly Ile Arg Ala Lys Trp Asp Ser Val Val
            340                 345                 350 ggc gac tgc cgg cag gag ttg gtg ttt atc ggc cag ggc ctc gac acc    1104
Gly Asp Cys Arg Gln Glu Leu Val Phe Ile Gly Gln Gly Leu Asp Thr
        355                 360                 365 gac gcg tta cag cgc gag ctc gac cac tgc ctg ctg agc gcc cag gaa    1152
Asp Ala Leu Gln Arg Glu Leu Asp His Cys Leu Leu Ser Ala Gln Glu
    370                 375                 380 atc gcc gcc ggc cca ctg gcc tgg caa gcg ctg cca ggg gcg acc gcc    1200
Ile Ala Ala Gly Pro Leu Ala Trp Gln Ala Leu Pro Gly Ala Thr Ala
385                 390                 395                 400 ttt gac cga cag acc ctt gcc cgc ccc cca cac agc cca tgg cga ttg    1248
Phe Asp Arg Gln Thr Leu Ala Arg Pro Pro His Ser Pro Trp Arg Leu
                405                 410                 415 ccc cca ttt gat ccg aga tag                                        1269
Pro Pro Phe Asp Pro Arg
            420

<210> SEQ ID NO 5
<211> LENGTH: 422
<212> TYPE: PRT
<213> ORGANISM: Pseudomonas marginalis

<400> SEQUENCE: 5

Met Thr Asp Gly Ala Gln Ala Ser Arg Leu Pro Val Thr Val Leu Ser
1               5                   10                  15
```

Gly Phe Leu Gly Ala Gly Lys Thr Thr Leu Asn His Ile Leu Arg
            20                  25                  30

Asn Arg Glu Gly Leu Arg Val Ala Val Ile Val Asn Asp Met Ser Glu
         35                  40                  45

Val Asn Ile Asp Ala Glu Glu Val Gln Arg Asp Val Ala Leu His Arg
 50                  55                  60

Gly Arg Asp Glu Leu Ile Glu Met Ser Asn Gly Cys Ile Cys Cys Thr
 65                  70                  75                  80

Leu Arg Ala Asp Leu Leu Glu Gln Ile Ser Met Leu Ala Arg Gln Gln
                 85                  90                  95

Arg Phe Asp Tyr Leu Leu Ile Glu Ser Thr Gly Ile Ser Glu Pro Met
            100                 105                 110

Pro Val Ala Glu Thr Phe Ala Phe Leu Asp Ala Asp Gly Phe Ser Leu
        115                 120                 125

Ser Glu Leu Ala Arg Leu Asp Thr Leu Val Thr Val Asp Gly Ser
    130                 135                 140

Arg Phe Gln Glu Leu Leu Glu Ser Pro His Thr Val Asp Gln Asp Asp
145                 150                 155                 160

Ala Thr Pro Asp Ala Pro Lys Arg His Leu Ala Asp Leu Leu Ile Glu
                165                 170                 175

Gln Val Glu Tyr Ala Asn Val Ile Leu Val Asn Lys Leu Asp Leu Ile
            180                 185                 190

Asp Ala Ala Gln Tyr Gln Ala Val Gln Ala Ile Leu Thr Gly Leu Asn
        195                 200                 205

Pro Thr Ala Arg Ile Met Pro Met Ala His Gly Asn Ile Pro Ser Ala
    210                 215                 220

Ser Leu Leu Gly Thr His Leu Phe Asp Leu Pro Ser Leu Ala Ala Ser
225                 230                 235                 240

Pro Gly Trp Met Arg Lys Met Glu Ala Ala Asp Ala Pro Ala Ser Glu
                245                 250                 255

Ser Asp Thr Tyr Gly Val Thr Ser Trp Val Tyr Arg Glu Arg Ala Pro
            260                 265                 270

Phe His Pro Gln Arg Leu Leu Asp Phe Leu Gln Gln Pro Trp Cys Asn
        275                 280                 285

Gly Arg Leu Leu Arg Ser Lys Gly Tyr Phe Trp Leu Ala Ser Arg His
    290                 295                 300

Leu Glu Thr Gly Leu Leu Val Gln Ser Gly Lys Arg Phe Gln Trp Asp
305                 310                 315                 320

Tyr Val Gly Arg Trp Trp Asn Phe Ile Glu Pro Ser Gln Trp Pro Arg
                325                 330                 335

Asp Glu Tyr Arg Leu Gln Gly Ile Arg Ala Lys Trp Asp Ser Val Val
            340                 345                 350

Gly Asp Cys Arg Gln Glu Leu Val Phe Ile Gly Gln Gly Leu Asp Thr
        355                 360                 365

Asp Ala Leu Gln Arg Glu Leu Asp His Cys Leu Leu Ser Ala Gln Glu
    370                 375                 380

Ile Ala Ala Gly Pro Leu Ala Trp Gln Ala Leu Pro Gly Ala Thr Ala
385                 390                 395                 400

Phe Asp Arg Gln Thr Leu Ala Arg Pro Pro His Ser Pro Trp Arg Leu
                405                 410                 415

Pro Pro Phe Asp Pro Arg
            420

<210> SEQ ID NO 6

```
<211> LENGTH: 2371
<212> TYPE: DNA
<213> ORGANISM: Pseudomonas putida
<220> FEATURE:
<221> NAME/KEY: CDS
<222> LOCATION: (1)..(582)
<223> OTHER INFORMATION: Coding region of alpha-subunit gene
<220> FEATURE:
<221> NAME/KEY: CDS
<222> LOCATION: (624)..(1286)
<223> OTHER INFORMATION: Coding region of beta-subunit gene
<220> FEATURE:
<221> NAME/KEY: gene
<222> LOCATION: (1283)..(2371)
<223> OTHER INFORMATION: Gene of activator protein

<400> SEQUENCE: 6
```

| | | | | | | | | | | | | | | | | |
|---|---|---|---|---|---|---|---|---|---|---|---|---|---|---|---|---|
| atg | acg | gca | act | tca | acc | cct | ggt | gag | cgg | gca | cgc | gca | ttg | ttt | gca | 48 |
| Met | Thr | Ala | Thr | Ser | Thr | Pro | Gly | Glu | Arg | Ala | Arg | Ala | Leu | Phe | Ala | |
| 1 | | | | 5 | | | | | 10 | | | | | 15 | | |
| gtg | ctc | aag | cgc | aaa | gac | ctc | atc | ccc | gag | ggc | tac | atc | gaa | cag | ctc | 96 |
| Val | Leu | Lys | Arg | Lys | Asp | Leu | Ile | Pro | Glu | Gly | Tyr | Ile | Glu | Gln | Leu | |
| | | | 20 | | | | | 25 | | | | | 30 | | | |
| acc | cag | ctg | atg | gaa | cac | ggc | tgg | agc | ccg | gaa | aac | ggc | gcg | cgc | atc | 144 |
| Thr | Gln | Leu | Met | Glu | His | Gly | Trp | Ser | Pro | Glu | Asn | Gly | Ala | Arg | Ile | |
| | | | 35 | | | | | 40 | | | | | 45 | | | |
| gtc | gcc | aag | gcc | tgg | gtc | gat | ccg | cag | ttt | cgc | gag | ctg | ctc | ctc | aag | 192 |
| Val | Ala | Lys | Ala | Trp | Val | Asp | Pro | Gln | Phe | Arg | Glu | Leu | Leu | Leu | Lys | |
| | 50 | | | | | 55 | | | | | 60 | | | | | |
| gac | ggt | acg | gcc | gcc | tgc | gcc | cag | ttc | ggc | ttc | acc | ggc | cca | caa | ggc | 240 |
| Asp | Gly | Thr | Ala | Ala | Cys | Ala | Gln | Phe | Gly | Phe | Thr | Gly | Pro | Gln | Gly | |
| 65 | | | | | 70 | | | | | 75 | | | | | 80 | |
| gaa | tac | atc | gtc | gcc | ctg | gaa | gac | acc | ccg | cag | ttg | aaa | aac | gtg | atc | 288 |
| Glu | Tyr | Ile | Val | Ala | Leu | Glu | Asp | Thr | Pro | Gln | Leu | Lys | Asn | Val | Ile | |
| | | | | 85 | | | | | 90 | | | | | 95 | | |
| gtc | tgt | agc | ctg | tgc | tcc | tgc | acg | aac | tgg | ccg | gtg | ctg | ggc | ctg | cca | 336 |
| Val | Cys | Ser | Leu | Cys | Ser | Cys | Thr | Asn | Trp | Pro | Val | Leu | Gly | Leu | Pro | |
| | | | 100 | | | | | 105 | | | | | 110 | | | |
| cct | gag | tgg | tac | aag | ggc | ttc | gag | ttc | cgt | gcg | cgg | ttg | gtc | cgg | gag | 384 |
| Pro | Glu | Trp | Tyr | Lys | Gly | Phe | Glu | Phe | Arg | Ala | Arg | Leu | Val | Arg | Glu | |
| | | | 115 | | | | | 120 | | | | | 125 | | | |
| ggg | cgc | acg | gta | ttg | cgc | gag | ctg | ggc | acc | gag | ttg | ccc | ggc | gac | atg | 432 |
| Gly | Arg | Thr | Val | Leu | Arg | Glu | Leu | Gly | Thr | Glu | Leu | Pro | Gly | Asp | Met | |
| | 130 | | | | | 135 | | | | | 140 | | | | | |
| gtg | gtc | aag | gtc | tgg | gac | acc | agc | gct | gaa | agc | cgc | tac | ctg | gtg | ctg | 480 |
| Val | Val | Lys | Val | Trp | Asp | Thr | Ser | Ala | Glu | Ser | Arg | Tyr | Leu | Val | Leu | |
| 145 | | | | | 150 | | | | | 155 | | | | | 160 | |
| ccg | caa | cga | cca | gcg | ggc | tca | gag | cat | atg | agc | gaa | gag | cag | ttg | cgg | 528 |
| Pro | Gln | Arg | Pro | Ala | Gly | Ser | Glu | His | Met | Ser | Glu | Glu | Gln | Leu | Arg | |
| | | | | 165 | | | | | 170 | | | | | 175 | | |
| caa | ctg | gtc | acc | aag | gac | gtg | ctg | atc | ggc | gtc | gcc | ctg | ccc | cgc | gtt | 576 |
| Gln | Leu | Val | Thr | Lys | Asp | Val | Leu | Ile | Gly | Val | Ala | Leu | Pro | Arg | Val | |
| | | | 180 | | | | | 185 | | | | | 190 | | | |
| ggc | tga | gcaaggccgc | ccaaccccat | tcaacttccg | gagtgttcaa | t atg | gat | ggc | | | | | | | | 632 |
| Gly | | | | | | Met | Asp | Gly | | | | | | | | |
| 195 | | | | | | | | | | | | | | | | |
| ttt | cac | gat | ctc | ggc | ggt | ttc | cag | ggc | ttt | ggc | aaa | gtg | ccc | cac | cgc | 680 |
| Phe | His | Asp | Leu | Gly | Gly | Phe | Gln | Gly | Phe | Gly | Lys | Val | Pro | His | Arg | |
| | | | 200 | | | | | 205 | | | | | 210 | | | |
| atc | aac | agc | ctg | agc | tac | aag | cag | gtg | ttc | aag | cag | gac | tgg | gaa | cac | 728 |
| Ile | Asn | Ser | Leu | Ser | Tyr | Lys | Gln | Val | Phe | Lys | Gln | Asp | Trp | Glu | His | |
| | | | | 215 | | | | | 220 | | | | | 225 | | |
| ctg | gcc | tac | agc | ctg | atg | ttc | atc | ggc | gtc | gac | cac | ctg | aac | aag | ttc | 776 |
| Leu | Ala | Tyr | Ser | Leu | Met | Phe | Ile | Gly | Val | Asp | His | Leu | Asn | Lys | Phe | |

```
                  230                 235                 240
agc gtc gac gaa ata cgt cat gcc gtc gaa cgc att gac gtg cgc cag    824
Ser Val Asp Glu Ile Arg His Ala Val Glu Arg Ile Asp Val Arg Gln
245                 250                 255                 260 cac gtc ggc acc gaa tac tac gaa cgt tat gtg atc gcc act gcc acg    872
His Val Gly Thr Glu Tyr Tyr Glu Arg Tyr Val Ile Ala Thr Ala Thr
                    265                 270                 275 ctg ctg gtc gaa aca ggc gtc atc acc cag gcc gaa ctg gat gaa gca    920
Leu Leu Val Glu Thr Gly Val Ile Thr Gln Ala Glu Leu Asp Glu Ala
                280                 285                 290 ctc ggc tcg cac ttc aag ctg gcc aac ccc gcc cat gcg caa ggg cgt    968
Leu Gly Ser His Phe Lys Leu Ala Asn Pro Ala His Ala Gln Gly Arg
            295                 300                 305 gct gca att atc ggg cga gcg cct ttt gaa gtg ggc gat cgg gtc atc   1016
Ala Ala Ile Ile Gly Arg Ala Pro Phe Glu Val Gly Asp Arg Val Ile
        310                 315                 320 gta cgc gat gaa tac gtg gcc ggg cat gtg cgc atg cct gca tac gtg   1064
Val Arg Asp Glu Tyr Val Ala Gly His Val Arg Met Pro Ala Tyr Val
325                 330                 335                 340 cgc ggc aag caa ggc gta gtg ctg cac cgg acc act gaa cag tgg ccg   1112
Arg Gly Lys Gln Gly Val Val Leu His Arg Thr Thr Glu Gln Trp Pro
                    345                 350                 355 ttt ccg gac gcg att ggc cat ggc gac cag agc gct gcg cat caa ccg   1160
Phe Pro Asp Ala Ile Gly His Gly Asp Gln Ser Ala Ala His Gln Pro
                360                 365                 370 acc tac cat gtc gag ttc cgc gtg cgg gac ctg tgg ggc gat gcc gca   1208
Thr Tyr His Val Glu Phe Arg Val Arg Asp Leu Trp Gly Asp Ala Ala
            375                 380                 385 gac gac ggc ctg gtg gtg gta gac ctg ttc gaa agc tat ctg gac agg   1256
Asp Asp Gly Leu Val Val Val Asp Leu Phe Glu Ser Tyr Leu Asp Arg
        390                 395                 400 gtc gaa agc ccg cga gtg gtg cgc gca tga gtgccggcgc ccaggcaggc     1306
Val Glu Ser Pro Arg Val Val Arg Ala
405                 410 cggctgccgg tgacggtcct ttcaggcttc ctcggcgcag gcaagaccac cctgctcaac 1366
cacatcctgc gcaaccgcca gggcctgaag gtggcggtta tcgtcaatga catgagcgag 1426
gtcaacatcg atgccgccca ggtccagcgc gacgttgcgc tgtatcgtgg ccaggatgaa 1486
ttgatagaga tgagcaacgg ctgtatctgc tgcaccctgc gcgccgacct gcttgagcag 1546
atcagcgcgc tggcgcgcca gcagcgtttc gattacctgt tgatcgagtc caccgggatt 1606
tccgagccga tgccagtcgc cgagacccttt gcctttctcg acgccaacgg tttcagcctc 1666
agcgaactgg cgcggctgga tacgctggtg acggtggtcg atgccagcca gttcatggcc 1726
atgctcgact ctcccgaaac cgtcgcgcgg gccgacgtca ccacggatga cagcaggcgc 1786
ccgctggccg atctgctgat cgagcaggtc gagtatgcca atgtgattct ggtcaacaaa 1846
cgcgacctgg tcgacgaggc gcagtaccag gccctgcagg cagttctcgc cgggctcaat 1906
ccaggcgcac agatcctgcc gatggtggcc ggcaacgtcg ccctgtcgag cgtccttggt 1966
acccagctgt tcgatttgcc cagccttgcc gcagcgcccg gctggatgaa acagatggac 2026
gcgcacgaca ccccggccgg cgagtcgcag acctatggcg tgacgtcatg ggtgtaccga 2086
gcgcgcgccc cgttccatcc gcaacgcttg cttgattttc tcgcccggcc ctggcgcgac 2146
ggccgtcttc tgcgcagcaa aggttatttc tggcttgcca gccgccaccg cgaaatcggc 2206
ttgctggtac acagcggcca gcagtttcaa tgggactatg ttggccattg gtggaacttc 2266
atcgacacgt cacagtggcc acaggacaag tatcgcttgc agggcatcat ggccaagtgg 2326
```

```
gacagcatcg tcggcgactg ccgacaggag ctgaaaagct tatga            2371
```

<210> SEQ ID NO 7
<211> LENGTH: 193
<212> TYPE: PRT
<213> ORGANISM: Pseudomonas putida
<400> SEQUENCE: 7

```
Met Thr Ala Thr Ser Thr Pro Gly Glu Arg Ala Arg Ala Leu Phe Ala
1               5                   10                  15

Val Leu Lys Arg Lys Asp Leu Ile Pro Glu Gly Tyr Ile Glu Gln Leu
            20                  25                  30

Thr Gln Leu Met Glu His Gly Trp Ser Pro Glu Asn Gly Ala Arg Ile
        35                  40                  45

Val Ala Lys Ala Trp Val Asp Pro Gln Phe Arg Glu Leu Leu Leu Lys
    50                  55                  60

Asp Gly Thr Ala Ala Cys Ala Gln Phe Gly Phe Thr Gly Pro Gln Gly
65                  70                  75                  80

Glu Tyr Ile Val Ala Leu Glu Asp Thr Pro Gln Leu Lys Asn Val Ile
                85                  90                  95

Val Cys Ser Leu Cys Ser Cys Thr Asn Trp Pro Val Leu Gly Leu Pro
            100                 105                 110

Pro Glu Trp Tyr Lys Gly Phe Glu Phe Arg Ala Arg Leu Val Arg Glu
        115                 120                 125

Gly Arg Thr Val Leu Arg Glu Leu Gly Thr Glu Leu Pro Gly Asp Met
130                 135                 140

Val Val Lys Val Trp Asp Thr Ser Ala Glu Ser Arg Tyr Leu Val Leu
145                 150                 155                 160

Pro Gln Arg Pro Ala Gly Ser Glu His Met Ser Glu Glu Gln Leu Arg
                165                 170                 175

Gln Leu Val Thr Lys Asp Val Leu Ile Gly Val Ala Leu Pro Arg Val
            180                 185                 190

Gly
```

<210> SEQ ID NO 8
<211> LENGTH: 220
<212> TYPE: PRT
<213> ORGANISM: Pseudomonas putida
<400> SEQUENCE: 8

```
Met Asp Gly Phe His Asp Leu Gly Gly Phe Gln Gly Phe Gly Lys Val
1               5                   10                  15

Pro His Arg Ile Asn Ser Leu Ser Tyr Lys Gln Val Phe Lys Gln Asp
            20                  25                  30

Trp Glu His Leu Ala Tyr Ser Leu Met Phe Ile Gly Val Asp His Leu
        35                  40                  45

Asn Lys Phe Ser Val Asp Glu Ile Arg His Ala Val Glu Arg Ile Asp
    50                  55                  60

Val Arg Gln His Val Gly Thr Glu Tyr Tyr Glu Arg Tyr Val Ile Ala
65                  70                  75                  80

Thr Ala Thr Leu Leu Val Glu Thr Gly Val Ile Thr Gln Ala Glu Leu
                85                  90                  95

Asp Glu Ala Leu Gly Ser His Phe Lys Leu Ala Asn Pro Ala His Ala
            100                 105                 110

Gln Gly Arg Ala Ala Ile Ile Gly Arg Ala Pro Phe Glu Val Gly Asp
        115                 120                 125
```

```
Arg Val Ile Val Arg Asp Glu Tyr Val Ala Gly His Val Arg Met Pro
        130                 135                 140

Ala Tyr Val Arg Gly Lys Gln Gly Val Val Leu His Arg Thr Thr Glu
145                 150                 155                 160

Gln Trp Pro Phe Pro Asp Ala Ile Gly His Gly Asp Gln Ser Ala Ala
                165                 170                 175

His Gln Pro Thr Tyr His Val Glu Phe Arg Val Arg Asp Leu Trp Gly
            180                 185                 190

Asp Ala Ala Asp Asp Gly Leu Val Val Asp Leu Phe Glu Ser Tyr
        195                 200                 205

Leu Asp Arg Val Glu Ser Pro Arg Val Val Arg Ala
    210                 215                 220

<210> SEQ ID NO 9
<211> LENGTH: 1089
<212> TYPE: DNA
<213> ORGANISM: Pseudomonas putida
<220> FEATURE:
<221> NAME/KEY: CDS
<222> LOCATION: (1)..(1089)
<223> OTHER INFORMATION: Coding region of activator protein gene

<400> SEQUENCE: 9 atg agt gcc ggc gcc cag gca ggc cgg ctg ccg gtg acg gtc ctt tca     48
Met Ser Ala Gly Ala Gln Ala Gly Arg Leu Pro Val Thr Val Leu Ser
1               5                   10                  15 ggc ttc ctc ggc gca ggc aag acc acc ctg ctc aac cac atc ctg cgc     96
Gly Phe Leu Gly Ala Gly Lys Thr Thr Leu Leu Asn His Ile Leu Arg
            20                  25                  30 aac cgc cag ggc ctg aag gtg gcg gtt atc gtc aat gac atg agc gag    144
Asn Arg Gln Gly Leu Lys Val Ala Val Ile Val Asn Asp Met Ser Glu
        35                  40                  45 gtc aac atc gat gcc gcc cag gtc cag cgc gac gtt gcg ctg tat cgt    192
Val Asn Ile Asp Ala Ala Gln Val Gln Arg Asp Val Ala Leu Tyr Arg
    50                  55                  60 ggc cag gat gaa ttg ata gag atg agc aac ggc tgt atc tgc tgc acc    240
Gly Gln Asp Glu Leu Ile Glu Met Ser Asn Gly Cys Ile Cys Cys Thr
65                  70                  75                  80 ctg cgc gcc gac ctg ctt gag cag atc agc gcg ctg gcg cgc cag cag    288
Leu Arg Ala Asp Leu Leu Glu Gln Ile Ser Ala Leu Ala Arg Gln Gln
                85                  90                  95 cgt ttc gat tac ctg ttg atc gag tcc acc ggg att tcc gag ccg atg    336
Arg Phe Asp Tyr Leu Leu Ile Glu Ser Thr Gly Ile Ser Glu Pro Met
            100                 105                 110 cca gtc gcc gag acc ttt gcc ttt ctc gac gcc aac ggt ttc agc ctc    384
Pro Val Ala Glu Thr Phe Ala Phe Leu Asp Ala Asn Gly Phe Ser Leu
        115                 120                 125 agc gaa ctg gcg cgg ctg gat acg ctg gtg acg gtg gtc gat gcc agc    432
Ser Glu Leu Ala Arg Leu Asp Thr Leu Val Thr Val Val Asp Ala Ser
    130                 135                 140 cag ttc atg gcc atg ctc gac tct ccc gaa acc gtc gcg cgg gcc gac    480
Gln Phe Met Ala Met Leu Asp Ser Pro Glu Thr Val Ala Arg Ala Asp
145                 150                 155                 160 gtc acc acg gat gac agc agg cgc ccg ctg gcc gat ctg ctg atc gag    528
Val Thr Thr Asp Asp Ser Arg Arg Pro Leu Ala Asp Leu Leu Ile Glu
                165                 170                 175 cag gtc gag tat gcc aat gtg att ctg gtc aac aaa cgc gac ctg gtc    576
Gln Val Glu Tyr Ala Asn Val Ile Leu Val Asn Lys Arg Asp Leu Val
            180                 185                 190 gac gag gcg cag tac cag gcc ctg cag gca gtt ctc gcc ggg ctc aat    624
Asp Glu Ala Gln Tyr Gln Ala Leu Gln Ala Val Leu Ala Gly Leu Asn
```

```
                195                 200                 205
cca ggc gca cag atc ctg ccg atg gtg gcc ggc aac gtc gcc ctg tcg        672
Pro Gly Ala Gln Ile Leu Pro Met Val Ala Gly Asn Val Ala Leu Ser
    210                 215                 220 agc gtc ctt ggt acc cag ctg ttc gat ttg ccc agc ctt gcc gca gcg        720
Ser Val Leu Gly Thr Gln Leu Phe Asp Leu Pro Ser Leu Ala Ala Ala
225                 230                 235                 240 ccc ggc tgg atg aaa cag atg gac gcg cac gac acc ccg gcc ggc gag        768
Pro Gly Trp Met Lys Gln Met Asp Ala His Asp Thr Pro Ala Gly Glu
                245                 250                 255 tcg cag acc tat ggc gtg acg tca tgg gtg tac cga gcg cgc gcc ccg        816
Ser Gln Thr Tyr Gly Val Thr Ser Trp Val Tyr Arg Ala Arg Ala Pro
    260                 265                 270 ttc cat ccg caa cgc ttg ctt gat ttt ctc gcc cgg ccc tgg cgc gac        864
Phe His Pro Gln Arg Leu Leu Asp Phe Leu Ala Arg Pro Trp Arg Asp
275                 280                 285 ggc cgt ctt ctg cgc agc aaa ggt tat ttc tgg ctt gcc agc cgc cac        912
Gly Arg Leu Leu Arg Ser Lys Gly Tyr Phe Trp Leu Ala Ser Arg His
                290                 295                 300 cgc gaa atc ggc ttg ctg gta cac agc ggc cag cag ttt caa tgg gac        960
Arg Glu Ile Gly Leu Leu Val His Ser Gly Gln Gln Phe Gln Trp Asp
305                 310                 315                 320 tat gtt ggc cat tgg tgg aac ttc atc gac acg tca cag tgg cca cag       1008
Tyr Val Gly His Trp Trp Asn Phe Ile Asp Thr Ser Gln Trp Pro Gln
                325                 330                 335 gac aag tat cgc ttg cag ggc atc atg gcc aag tgg gac agc atc gtc       1056
Asp Lys Tyr Arg Leu Gln Gly Ile Met Ala Lys Trp Asp Ser Ile Val
    340                 345                 350 ggc gac tgc cga cag gag ctg aaa agc tta tga                           1089
Gly Asp Cys Arg Gln Glu Leu Lys Ser Leu
        355                 360

<210> SEQ ID NO 10
<211> LENGTH: 362
<212> TYPE: PRT
<213> ORGANISM: Pseudomonas putida

<400> SEQUENCE: 10

Met Ser Ala Gly Ala Gln Ala Gly Arg Leu Pro Val Thr Val Leu Ser
1               5                   10                  15

Gly Phe Leu Gly Ala Gly Lys Thr Thr Leu Leu Asn His Ile Leu Arg
            20                  25                  30

Asn Arg Gln Gly Leu Lys Val Ala Val Ile Val Asn Asp Met Ser Glu
        35                  40                  45

Val Asn Ile Asp Ala Ala Gln Val Gln Arg Asp Val Ala Leu Tyr Arg
    50                  55                  60

Gly Gln Asp Glu Leu Ile Glu Met Ser Asn Gly Cys Ile Cys Cys Thr
65                  70                  75                  80

Leu Arg Ala Asp Leu Leu Glu Gln Ile Ser Ala Leu Ala Arg Gln Gln
                85                  90                  95

Arg Phe Asp Tyr Leu Leu Ile Glu Ser Thr Gly Ile Ser Glu Pro Met
            100                 105                 110

Pro Val Ala Glu Thr Phe Ala Phe Leu Asp Ala Asn Gly Phe Ser Leu
        115                 120                 125

Ser Glu Leu Ala Arg Leu Asp Thr Leu Val Thr Val Asp Ala Ser
    130                 135                 140

Gln Phe Met Ala Met Leu Asp Ser Pro Glu Thr Val Ala Arg Ala Asp
145                 150                 155                 160
```

```
Val Thr Thr Asp Asp Ser Arg Arg Pro Leu Ala Asp Leu Leu Ile Glu
            165                 170                 175

Gln Val Glu Tyr Ala Asn Val Ile Leu Val Asn Lys Arg Asp Leu Val
        180                 185                 190

Asp Glu Ala Gln Tyr Gln Ala Leu Gln Ala Val Leu Ala Gly Leu Asn
    195                 200                 205

Pro Gly Ala Gln Ile Leu Pro Met Val Ala Gly Asn Val Ala Leu Ser
210                 215                 220

Ser Val Leu Gly Thr Gln Leu Phe Asp Leu Pro Ser Leu Ala Ala Ala
225                 230                 235                 240

Pro Gly Trp Met Lys Gln Met Asp Ala His Asp Thr Pro Ala Gly Glu
                245                 250                 255

Ser Gln Thr Tyr Gly Val Thr Ser Trp Val Tyr Arg Ala Arg Ala Pro
            260                 265                 270

Phe His Pro Gln Arg Leu Leu Asp Phe Leu Ala Arg Pro Trp Arg Asp
        275                 280                 285

Gly Arg Leu Leu Arg Ser Lys Gly Tyr Phe Trp Leu Ala Ser Arg His
    290                 295                 300

Arg Glu Ile Gly Leu Leu Val His Ser Gly Gln Gln Phe Gln Trp Asp
305                 310                 315                 320

Tyr Val Gly His Trp Trp Asn Phe Ile Asp Thr Ser Gln Trp Pro Gln
                325                 330                 335

Asp Lys Tyr Arg Leu Gln Gly Ile Met Ala Lys Trp Asp Ser Ile Val
            340                 345                 350

Gly Asp Cys Arg Gln Glu Leu Lys Ser Leu
            355                 360

<210> SEQ ID NO 11
<211> LENGTH: 30
<212> TYPE: DNA
<213> ORGANISM: Artificial Sequence
<220> FEATURE:
<223> OTHER INFORMATION: Primer 1F

<400> SEQUENCE: 11
ctccaccata tgagtacagc tacttcaacg                                      30

<210> SEQ ID NO 12
<211> LENGTH: 30
<212> TYPE: DNA
<213> ORGANISM: Artificial Sequence
<220> FEATURE:
<223> OTHER INFORMATION: Primer 1R

<400> SEQUENCE: 12
cttcataagc ttctatctcg gatcaaatgg                                      30

<210> SEQ ID NO 13
<211> LENGTH: 25
<212> TYPE: DNA
<213> ORGANISM: Artificial Sequence
<220> FEATURE:
<223> OTHER INFORMATION: Primer 2F

<400> SEQUENCE: 13
atgacggcaa cttcaacccc tggtg                                           25

<210> SEQ ID NO 14
<211> LENGTH: 20
<212> TYPE: DNA
<213> ORGANISM: Artificial Sequence
```

```
<220> FEATURE:
<223> OTHER INFORMATION: Primer 2R

<400> SEQUENCE: 14
tcagctcctg tcggcagtcg                                              20
```

POLYNUCLEOTIDES WHICH CODE FOR CYANIDE-TOLERANT NITRILE HYDRATASE AND COMPOSITIONS THEREOF

CROSS REFERENCE TO RELATED APPLICATION DATA

This application is a divisional of U.S. patent application Ser. No. 10/598,873, filed 14 Sep. 2006, now U.S. Pat. No. 7,592,165, which is a 371 of PCT/EP05/02689, filed 14 Mar. 2005. This application also claims the benefit of PCT/EP05/02689 and DE 10 2004 013 847.9, filed 20 Mar. 2004. U.S. patent application Ser. No. 10/598,873 is incorporated by reference in its entirety.

BACKGROUND OF THE INVENTION

1. Field of the Invention

The invention relates to cyanide-tolerant nitrile hydratases especially from *Pseudomonas putida* or *Pseudomonas marginalis* strains which exhibit increased cyanide tolerance, to their use for preparing amides from nitriles in the presence of cyanides and to polynucleotide sequences coding for this enzyme.

2. Description of the Related Art

The conversion of α-hydroxy nitriles (cyanohydrins) and α-amino nitriles into the corresponding amides using nitrile hydratases opens up a novel variant for synthesizing α-hydroxy acids and α-amino acids because α-hydroxy amides and α-amino amides can be hydrolyzed in a simple manner (Process and catalysts for the production of methionine. Ponceblanc, Herve; Rossi, Jean-Christophe; Laval, Philip; Gros, Georges. (Rhone-Poulenc Animal Nutrition SA, Fr.), (WO 2001060789). Alternatively, α-hydroxy amides can also be reacted with alkali metal or alkaline earth metal hydroxides to give the corresponding salts of the hydroxy acids. A particularly preferred reaction in this connection is that of 4-methylthio-α-hydroxybutyramide (MHA amide) with calcium hydroxide, because calcium MHA can be employed directly as alternative form of product to methionine or MHA as feed additive.

However, α-hydroxy nitriles and α-amino nitriles readily decompose to aldehydes and hydrocyanic acid, and aldehydes, hydrocyanic acid and ammonia, respectively. The resulting hydrocyanic acid is a strong inhibitor of almost all known nitrile hydratases with the exception of the nitrile hydratase from *Rhodococcus equi* XL-1, which shows the smallest loss of activity known to date at 20 mM cyanide (Production of amides from nitriles by *Rhodococcus equi* cells having a cyanide resistant-nitrile hydratase. Nagasawa, Tohru; Matsuyama, Akinobu. (Daicel Chemical Industries, Ltd., Japan), (EP 1 266 962 A).

The low productivity of about 8 g of amide per g of dry biomass of resting cells, the long reaction time of 43 hours and the relatively low product concentration of 75 g/l lead to the search for improved nitrile hydratases.

SUMMARY OF THE INVENTION

The aim of the invention described herein is therefore to provide a biocatalyst which is not subject to these restrictions. In addition, an even greater tolerance of cyanide by the biocatalyst is advantageous, because α-hydroxy nitriles and α-amino nitriles are prepared, in order to ensure a rapid and complete reaction of the aldehyde, preferably with a 1-3% excess of hydrocyanic acid, part of which remains in the product. It is thus possible for cyanide concentrations exceeding 20 mM to occur during the biotransformation. By-products and reagents such as amines employed as auxiliary bases must likewise not inhibit the nitrile hydratase activity.

It is an object of the invention to provide nitrile hydratases which exhibit an increased stability to the cyanide ions present in the reaction solution during the conversion of nitriles to amides.

DETAILED DESCRIPTION OF THE DRAWINGS

Figure 7:
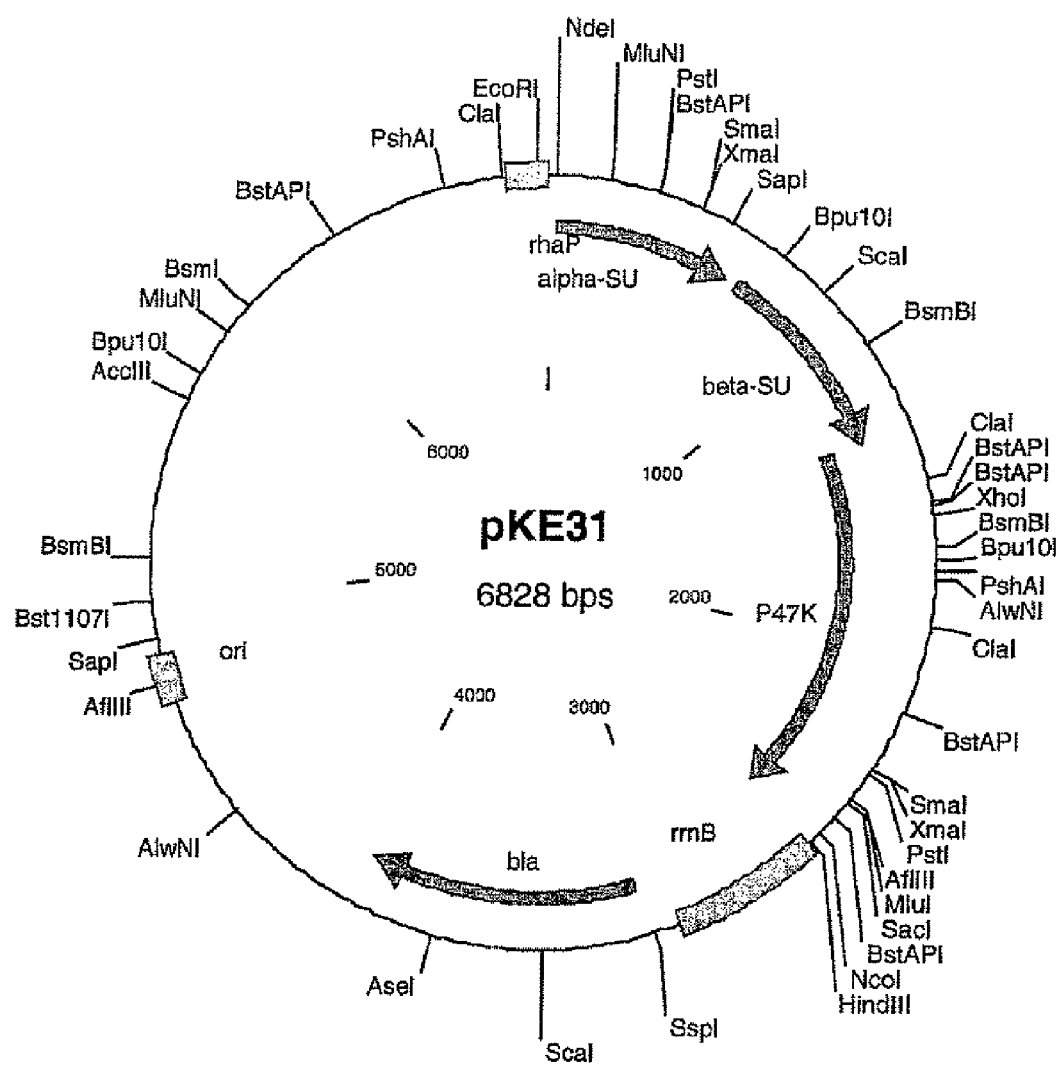

FIG. 7 schematically shows the restriction map of the expression vector pKE31.

DETAILED DESCRIPTION OF THE INVENTION

The invention relates to isolated polynucleotides, in particular from microorganisms of the genus *Pseudomonas*, which code for polypeptides having the amino acid sequences which are 90 to 100% identical to the amino acid sequences comprised in the sequences SEQ ID NO: 2, 3, 5, 7, 8, 10, where the polypeptides comprising the sequences SEQ ID NO: 2, 3, 5 or 7, 8, 10, together in each case have the activity of a cyanide-tolerant nitrile hydratase or form this nitrile hydratase.

The polynucleotides are preferably derived from *Pseudomonas putida* or *Pseudomonas marginalis*.

The invention further relates to polynucleotides selected from the group of
a) polynucleotides comprising or consisting of the nucleotide sequences from SEQ ID NO: 1, 4, 6, 9 or nucleotide sequences complementary thereto,
b) polynucleotides comprising nucleotide sequences which correspond to the sequences from a) within the scope of the degeneracy of the genetic code,
c) polynucleotides comprising nucleotide sequences as in a) which comprise functionally neutral sense mutations,
d) polynucleotides which hybridize with the complementary sequences from a) or c) under stringent conditions,
where the polynucleotides code for a cyanide-tolerant nitrile hydratase.

The invention likewise relates to the polypeptides encoded by these polynucleotides and having the sequences SEQ ID NO: 2, 3, 5 or 7, 8, 10 with the activity of cyanide-tolerant nitrile hydratases from microorganisms of the genus *Pseudomonas*, which may be present either enriched in the microorganisms or in isolated form. SEQ ID NO: 2 and 7 code for the alpha subunits of the nitrile hydratases, SEQ ID NO: 3 and 8 for the beta subunits of the nitrile hydratases and SEQ ID NO: 5 and 10 for activator proteins whose coexpression is essential for the activity of the nitrile hydratases (Nojiri et al., 1999, Journal of Biochemistry, 125: 696-704).

It is preferred according to the invention to use host cells which have been transformed or transfected by the polynucleotides of the invention.

The host cells may belong to the eukaryotes or prokaryotes for which a stable expression system is known, in particular the host organisms preferably used are microorganisms for which there are expression systems, such as, for example, *Pseudomonas, Pichia*, various yeasts, *Saccharomyces, Aspergillus* or the Streptomyces family, especially *E. coli*. Microorganisms of the genus *Rhodococcus* are likewise suitable.

Vector DNA can be introduced into eukaryotic or prokaryotic cells by known techniques of transformation or transfection.

"Transformation", "transfection", conjugation" and "transduction" refer to procedures known in the state of the arts for introducing foreign DNA.

The invention likewise relates to polynucleotides which consist essentially of one polynucleotide sequence, which are obtainable by screening by means of hybridization of an appropriate gene library of *Pseudomonas marginalis* or *Pseudomonas putida* which comprises the complete gene or parts thereof, with a probe which comprises the sequences of the polynucleotides of the invention from SEQ ID No: 1, 4 or 6, 9 or fragments thereof, and isolation of said polynucleotide sequence.

Polynucleotides which comprise the sequences of the invention are suitable as hybridization probes for RNA, cDNA and DNA in order to isolate full-length nucleic acids and polynucleotides or genes which code for the proteins of the invention, or in order to isolate those nucleic acids and polynucleotides or genes which exhibit a great similarity of the sequences to those of the genes of the invention. They can likewise be attached as probe to so-called arrays, microarrays or DNA chips in order to detect and determine the corresponding polynucleotides or sequences derived therefrom, such as, for example, RNA or cDNA.

Polynucleotides which comprise the sequences of the invention are further suitable as primers with whose aid it is possible with the polymerase chain reaction (PCR) to prepare DNA of genes which code for the proteins of the invention.

Such oligonucleotides serving as probes or primers comprise at least 25 or 30, preferably at least 20, very particularly preferably at least 15, consecutive nucleotides. Oligonucleotides having a length of at least 40 or 50 nucleotides are likewise suitable. Also suitable where appropriate are oligonucleotides having a length of at least 100, 150, 200, 250 or 300 nucleotides.

"Isolated" means separated from its natural environment.

"Polynucleotide" refers in general to polyribonucleotides and polydeoxyribonucleotides, possibilities being unmodified RNA or DNA or modified RNA or DNA.

The polynucleotides of the invention include polynucleotides of SEQ ID No: 1, 4, 6, 9 or fragments contained therein, and also those which are at least 90%, 93%, 95%, 97% or 99% identical to the polynucleotides of SEQ ID NO: 1, 4, 6, 9 or fragments contained therein.

"Polynucleotides" mean peptides or proteins which comprise two or more amino acids connected by peptide linkages.

The polypeptides of the invention include polypeptides of sequences SEQ ID NO: 2, 3, 5, 7, 8, 10, and also those which are at least 90%, and particularly preferably at least 91%, 95%, 97% or 99% identical to the polypeptides of sequences SEQ ID NO: 2, 3, 5, 7, 8, 10.

The DNA sequences obtained from the desired gene library can then be examined using known algorithms or sequence analysis programs such as, for example, that of Staden (Nucleic Acids Research 14, 217-232 (1986)), that of Marck (Nucleic Acids Research 16, 1829-1836 (1988)) or the GCG program of Butler (Methods of Biochemical Analysis 39, 74-97 (1998)).

Coding DNA sequences which are derived from the sequences comprised in SEQ ID No. 1, 4, 6, 9 through the degeneracy of the genetic code are likewise an aspect of the invention. In the same way, DNA sequences which hybridize with the sequences or parts thereof are an aspect of the invention. Also known to experts are conservative amino acid exchanges such as, for example, exchange of glycine for alanine or of aspartic acid for glutamic acid in proteins as "sense mutations" which do not lead to a fundamental change in the activity of the protein, i.e. are functionally neutral. It is further known that changes at the N or C terminus of a protein may not substantially impair or even stabilize its function. Details concerning this are to be found by a person skilled in the art inter alia in Ben-Bassat et al. (Journal of Bacteriology 169: 751-757 (1987)), in O'Regan et al. (Gene 77: 237-251 (1989)), in Sahin-Toth et al. (Protein Sciences 3: 240-247 (1994)), in Hochuli et al. (Bio/Technology 6: 1321-1325 (1988)) and in well-known textbooks of genetics and molecular biology.

Finally, DNA sequences which are prepared by the polymerase chain reaction (PCR) using primers which are derived from SEQ ID NO: 1, 4, 6, 9 are an aspect of the invention. Such oligonucleotides typically have a length of at least 15 consecutive nucleotides, in particular of 20, 30 or 40.

Instructions for the identification of DNA sequences by means of hybridization are to be found by a person skilled in the art inter alia in the handbook "The DIG System Users Guide for Filter Hybridization" of Boehringer Mannheim GmbH (Mannheim, Germany, 1993) and in Liebl. et al. (International Journal of Systematic Bacteriology (1991) 41: 255-260). The hybridization takes place under stringent conditions, meaning that only hybrids in which probe and target sequence, i.e. the polynucleotides treated with the probe, are at least 90% identical are formed. It is known that the stringency of the hybridization including the washing steps is influenced or determined by variation in the buffer composition, the temperature and the salt concentration. The hybridization reaction is preferably carried out with relatively low stringency compared with the washing steps (Hybaid Hybridisation Guide, Hybaid Limited, Teddington, UK, 1996).

It is possible to employ for the hybridization reaction for example a 5×SSC buffer at a temperature of about 50° C.-68° C. It is possible in this case also for probes to hybridize with polynucleotides exhibiting less than 70% identity to the sequence of the probe. Such hybrids are less stable and are removed by washing under stringent conditions. This can be achieved for example by lowering the salt concentration to 2×SSC and, where appropriate, subsequently 0.5×SSC (The DIG System User's Guide for Filter Hybridisation, Boehringer Mannheim, Mannheim, Germany, 1995), setting a temperature of about 50° C.-68° C. It is possible where appropriate to lower the salt concentration to a 0.1×SSC. It is possible by raising the hybridization temperature stepwise in steps of about 1-2° C. from 50° C. to 68° C. to isolate polynucleotide fragments which have, for example, at least 90% to 95% identity to the sequence of the probe employed. Further instructions for hybridization are obtainable on the market in the form of so-called kits (e.g. DIG Easy Hyb from Roche Diagnostics GmbH, Mannheim, Germany, Catalogue No. 1603558).

Instructions for the amplification of DNA sequences with the aid of the polymerase chain reaction (PCR) are to be found by a person skilled in the art inter alia in the handbook by Gait: Oligonukleotide synthesis: A Practical Approach (IRL Press, Oxford, UK, 1984) and in Newton and Graham: PCR (Spektrum Akademischer Verlag, Heidelberg, Germany, 1994).

The procedure is generally such that a gene which can be expressed well is cloned into a vector with lower copy number, genes with lower expression efficiency on a vector with higher copy number and/or strong promoter. The host cells are transformed with these vectors in such a way that, compared with the initial organism, they comprise at least in each case one additional copy of the nucleotide sequences coding for the formation of nitrile hydratase.

The transformed or recombinant microorganisms prepared in this way, especially of the genus *Pseudomonas*, are likewise part of the invention.

It has been found that enhancement of the genes coding for the nitril hydratase of the invention and the helper protein P47K in microorganisms leads to an increased production of the nitrile hydratase or else to an increased activity of the nitrile hydratase.

The term "enhancement" describes in this connection the increase in the intracellular activity of one or more enzymes in a microorganism which are encoded by the appropriate DNA by, for example, increasing the copy number of the gene or of the genes, using a strong promoter or using a gene which codes for a corresponding enzyme with a high activity and, where appropriate, combining these measures, compared with the non-recombinant initial organism.

To achieve overexpression it is possible to mutate the promoter and regulatory region or the ribosome binding site which is located upstream of the structural gene. Expression cassettes incorporated upstream of the structural gene work in the same way. It is additionally possible to increase expression during the fermentative amino acid production by inducible promoters. Expression is likewise improved by measures to extend the lifespan of the m-RNA.

In addition, the enzymatic activity is likewise enhanced by preventing degradation of the enzyme protein. The genes or gene constructs may be present either in plasmids with varying copy number or integrated and amplified in the chromosome. A further alternative possibility is to achieve overexpression of the relevant genes by modifying the composition of the media and management of the culturing.

The invention likewise relates to
1) a process for the enzymatic preparation of amides from nitriles, which comprises the following steps:
   a) conversion of a compound which comprises a nitrile group or nitrile groups using a microbial enzyme which has nitrile hydratase activity and
   b) removal of the amide formed, where
   c) a nitrile hydratase of the invention is employed for converting the nitrile into the amide. The remaining activity thereof after conversion of methacrylonitrile in the presence of 20 mM (mM=mmol/l) cyanide ions at 20° C. after 30 min is preferably at least 90% of the remaining activity of the same enzyme when it has been employed for the conversion in the absence of cyanide ions under conditions which are otherwise the same.
2) a process according to 1), characterized in that the remaining activity after the conversion in the presence of 50 mM cyanide ions is at least 60%,
3) a process according to 1) or 2), characterized in that microorganisms producing and containing enzyme, or the lysate thereof, is/are employed.
4) a process according to 3), characterized in that resting cell of the microorganism is employed,
5) a process according to 1) or 2), characterized in that the purified enzyme is employed,
6) a process according to 1) to 5), characterized in that the enzyme is derived from microorganisms of the genus *Pseudomonas*, in particular *Pseudomonas putida* or *Pseudomonas marginalis*,
7) a process according to 6, characterized in that the enzyme is derived from microorganisms of the genus *Pseudomonas* deposited under the numbers DSM 16275 and DSM 16276, and which have amino acid sequences having the sequences SEQ ID NO: 2, 3, 5, 7, 8, 10,
8) a process according to one or more of points 1) to 7), characterized in that compounds of the general formulae

in which the meanings are:
X: OH, H, alkyl having 1 to 4 C atoms, $NH_2$
R: H, saturated alkyl radical having 1 to 12 C atoms, branched or unbranched, optionally $NH_2$-substituted unsaturated alkyl radicals having a double bond and 1 to 12 C atoms, branched or unbranched, cycloalkyl groups having 3 to 6 C atoms,
alkylene radicals substituted by alkylthio groups, where alkyl here corresponds to a $C_1$ to $C_3$ radical,
and alkylene corresponds to a divalent $C_3$ to $C_8$ radical,
R': H, if R is not H, alkyl having 1 to 3 C atoms,
R": mono- or binuclear unsaturated ring having 6 to 12 C atoms, optionally substituted by one or two alkyl groups ($C_1$-$C_3$), Cl, Br, F, monovalent alkyl nitrile radical having 1 to 6 C atoms,
are converted to the corresponding amides,
9) a process according to 8), characterized in that a compound of the general formula (I) is converted in the presence of hydrocyanic acid or a salt of hydrocyanic acid,
10) a process according to 9), characterized in that the conversion is carried out in the presence of 0.1 mol % cyanide to 3 mol % cyanide based on the nitrile employed, preferably >2 to 3 mol %. This corresponds at a final concentration of 1 mol to 30 mMol of cyanide at 3 mol %,
11) a process according to one or more of points 1) to 10), characterized in that methionine nitrile is employed as nitrile,
12) a process according to one or more of points 1) to 10), characterized in that 2-hydroxy-4-methylthiobutyronitrile is employed as nitrile.
A reaction mixture like that obtained when hydrocyanic acid, 3-methylthiopropionaldehyde are reacted in the presence of an auxiliary base such as, for example, triethylamine according to the prior art is preferably employed.
It can advantageously be employed without purification.
This indicates the additional stability of the enzymes of the invention toward aldehydes and amines.
13) A process in which 2-hydroxy-2-methylpropionitrile is employed as precursor for methacrylamide.
14) The invention is likewise directed to isolated and purified microorganisms of the genus *Pseudomonas*, deposited under the numbers DSM 16275 (MA32, *Pseudomonas marginalis*) and DSM 16276 (MA113, *Pseudomonas putida*), and 15) cyanide-tolerant nitrile hydratases isolated from the strains of the genus *Pseudomonas*, in particular from the strains of *Pseudomonas putida* and *Pseudomonas marginalis* deposited under the numbers DSM 16275 and DSM 16276.

The deposition took place on Mar. 9, 2004, at the DSMZ, Deutsche Sammlung für Mikroorganismen und Zellkulturen in Brunswick, in accordance with the Budapest treaty.

The strains are particularly suitable for producing the enzymes of the invention.

"Isolated and purified microorganisms" relates to microorganisms which are present in a higher concentration than found naturally.

The invention likewise relates to a process for preparing the cyanide-tolerant nitrile hydratase described above, in which
a) a microorganism producing this nitrile hydratase, in particular of the genus *Pseudomonas marginalis* or *Pseudomonas putida*, is fermented under conditions with which the enzyme is formed in the microorganism, and
b) the cells are harvested at the earliest after the logarithmic growth phase has been completed.

Subsequently,
a) either the microorganism comprising the enzyme in the form of resting cells, where appropriate after increasing the permeability of the cell membrane, or
b) the lysate of the cells or
c) the enzyme isolated from the cells of the microorganism using known measures
is employed for the conversion according to the invention of nitriles into amides.

The nitrile hydratase may be either an enzyme generated with non-recombinant microorganisms or an enzyme generated recombinantly.

The invention additionally relates to processes for the recombinant preparation of the polypeptides of the invention, where a microorganism producing these polypeptides is cultivated, where appropriate expression of the relevant polynucleotides is induced, and the enzymes are isolated where appropriate from the culture.

The process is generally one in which
a) microorganisms in particular of the genera *Pseudomonas marginalis* or *Pseudomonas putida* in which isolated polynucleotides from microorganisms of the family *Pseudomonas* which code for polypeptides having the amino acid sequences which are 90 to 100% identical to the amino acid sequences comprising sequences in SEQ ID NO: 2, 3 and 5 or 7, 8 and 10, where the polypeptides in each case jointly have the activity of a cyanide-tolerant nitrile hydratase, enhanced, in particular recombinantly overexpressed, are fermented,
b) the enzyme having nitrile hydratase activity is isolated where appropriate from these microorganisms, or a protein fraction comprising this enzyme is prepared, and
c) the microorganism according to a) or the enzyme according to or the fraction comprising the latter b) is transferred into a medium which comprises a compound comprising nitrile groups of the general formulae (I) and (II).

The culture medium used for the fermentation must comply in a suitable manner with the demands of the respective strains. Descriptions of culture media of various microorganisms are present in the handbook "Manual of Methods for General Bacteriology" of the American Society for Bacteriology (Washington D.C., USA, 1981).

It is possible to use as carbon source sugars and carbohydrates such as, for example, glucose, sucrose, lactose, fructose, maltose, molasses, starch and cellulose, oils and fats such as, for example, soybean oil, sunflower oil, peanut oil and coconut fat, fatty acids such as, for example palmitic acid, stearic acid and linoleic acid, alcohols such as, for example, glycerol and ethanol and organic acids such as, for example, acetic acid. These substances can be used singly or as mixture.

It is possible advantageously to use as nitrogen source organic nitriles or amides such as acetonitrile, acetamide, methacrylonitriles, methacrylamide, isobutyronitrile, isobutyramide or urea also in combination with other nitrogen-containing compounds such as peptones, yeast extract, meat extract, malt extract, corn steep liquor, soybean flour and or inorganic compounds such as ammonium sulfate, ammonium chloride, ammonium phosphate, ammonium carbonate and ammonium nitrate. The nitrogen sources may be used singly or as mixture.

It is possible to use as phosphorus source phosphoric acid, potassium dihydrogen phosphate or dipotassium hydrogen phosphate or the corresponding sodium-containing salts. The culture medium must additionally comprise salts of metals, such as, for example, magnesium sulfate or iron sulfate, which are necessary for growth. Finally, essential growth factors such as amino acids and vitamins can be employed in addition to the abovementioned substances. Said starting materials can be added to the culture in the form of a single batch or be fed in during the cultivation in a suitable manner.

The pH of the culture is controlled in a suitable manner by employing basic compounds such as sodium hydroxide, potassium hydroxide, ammonia or aqueous ammonia or acidic compounds such as phosphoric acid or sulfuric acid. Foaming can be controlled by employing antifoams such as, for example, fatty acid polyglycol esters. Aerobic conditions are maintained by introducing oxygen or oxygen-containing gas mixtures such as, for example, air into the culture. The temperature of the culture is normally 10° C. to 40° C. and preferably 10° C. to 30° C. The culture is continued until it has passed through the logarithmic growth phase. This aim is normally achieved within 10 hours to 70 hours. Following this, the cells are preferably harvested, washed and taken up in a buffer as suspension at a pH of 6-9, in particular of 6.8 to 7.9. The cell concentration amounts to 1-25%, in particular 1.5 to (wet weight/v). The permeability can be increased by physical or chemical methods, e.g. with toluene as described in Wilms et al., J. Biotechnol., Vol. 86 (2001), 19-30, so that the nitrile to be converted can penetrate through the cell wall and the amide can emerge.

The following nitriles are preferably converted:
saturated mononitriles:
acetonitrile, propionitrile, butyronitrile, isobutyronitrile, valeronitrile, isovaleronitrile, capronitrile
saturated dinitriles:
malonitrile, succinonitrile, glutaronitrile, adiponitrile
aromatic unsubstituted and substituted mono- and dinitriles:
benzonitrile, 2,6-difluorobenzonitrile, phthalonitrile, isophthalonitrile, terephthalonitrile,
α-amino nitriles:
α-aminopropionitrile, α-aminomethylthiobutyronitrile, α-aminobutyronitrile, aminoacetonitrile, all nitriles derived from natural amino acids, α-amino-3,3-dimethylpropionitrile, α-amino-2,3-dimethylpropionitrile
nitriles with carboxyl groups:
cyanoacetic acid
β-amino nitriles:
3-aminopropionitril
unsaturated nitriles:
acrylonitrile, methacrylonitrile, allyl cyanide, crotononitrile α-hydroxy nitriles:
α-hydroxy-n-propionitrile, α-hydroxy-n-butyronitrile, α-hydroxyisobutyronitrile, α-hydroxy-n-hexanonitrile, α-hydroxy-n-heptanonitrile, α-hydroxy-n-octanonitrile, α,γ-dihydroxy-β,β-dimethylbutyronitrile, acrolein cyanohydrin, methacrylaldehyde cyanohydrin, 3-chlorolactonitrile, 4-methylthio-α-hydroxybutyronitrile and α-hydroxyphenylpropionitrile.

The concentration of the nitriles to be converted in the reaction solution is not limited to particular ranges.

In order to avoid inhibition of the enzymatic activity via the substrate, the concentration of the nitrile is generally maintained at 0.02 to 10 w/w %, in particular 0.1 to 2 w/w %, based on the amount of the biocatalyst as dry biomass. The substrate can be added as a whole at the start of the conversion or continuously or discontinuously during the conversion.

The dry weight is determined using the Moisture Analyser MA 45 (Sartorius).

If the solubility of the nitrile compound in the aqueous reaction system is too low, a solubilizer can be added.

The reaction may, however, alternatively also be carried out in a water/organic solvent two-phase system.

When the cells of the microorganism are used as enzymatically active material, the amount of the cells employed is preferably 0.02 to 10 w/w % as dried biomass in relation to the amount of substrate.

It is also possible for the isolated enzyme to be immobilized by generally known techniques and then to be employed in this form.

The reaction is generally carried out at temperatures from −5° C. to 50° C., in particular 0° C. to 30° C., and for a time of from 0.1 to 100 hours.

The pH of the reaction mixture which is to be maintained is not limited to particular values as long as the enzymatic activity is not impaired. After the conversion, the amide formed can be removed from the reaction solution as known and be purified.

The invention likewise relates to a process in which the amide or the solution comprising the amide is separated for example from the cells of the biomass, and the amide is either hydrolyzed to the corresponding acid or converted with addition of alkali metal or alkaline earth metal hydroxides to the corresponding salts of the acids. MHA amide is preferably hydrolyzed with calcium hydroxide and the corresponding calcium salt is isolated.

EXAMPLES

Example 1

Culturing Conditions

The precultures were grown in a volume of 5 ml in glass tubes, shaking at 30° C. over the course of 24 h. 100 ml of the main culture were inoculated with 1 ml of the preculture and shaken in an Erlenmeyer flask with a total volume of 1000 ml at 25° C. for 42 h.

| Medium for the preculture (pH 7.0) | |
|---|---|
| $K_2HPO_4$ | 7 g |
| $KH_2PO_4$ | 3 g |
| Na citrate | 0.5 g |
| Glycerol | 2 g |
| $FeSO_4 * 7 H_2O$ | 0.004 g |
| $MgSO4 * 7 H_2O$ | 0.1 g |
| Acetamide | 2 g |
| Trace salt solution | 0.1 ml |
| Demineralized water | Ad. 1000 ml |

| Medium for the main culture (pH 7.0) | |
|---|---|
| $K_2HPO_4$ | 7 g |
| $KH_2PO_4$ | 3 g |
| Sodium citrate | 0.5 g |
| Glycerol | 2 g |
| $FeSO_4 * 7 H_2O$ | 0.004 g |
| $MgSO4 * 7 H_2O$ | 0.1 g |
| Acetamide | 10 g |
| Trace salt solution | 0.1 ml |
| Demineralized water | Ad. 1000 ml |

| Trace salt solution | |
|---|---|
| EDTA, $Na_2 * 2 H_2O$ | 158 mg |
| $Na_2MoO_4 * 2 H_2O$ | 4.7 mg |
| $ZnSO_4 * 7 H_2O$ | 70 mg |
| $MnSO_4 * 4 H_2O$ | 18 mg |
| $FeSO_4 * 7 H_2O$ | 16 mg |
| $CuSO_4 * 5 H_2O$ | 4.7 mg |
| $CoSO_4 * 6 H_2O$ | 5.2 mg |
| Demineralized water | Ad. 1000 ml |

Example 2

Isolation and Identification of the Microorganisms

The two strains MA32 and MA113 were selected by determining the nitrile hydratase activity of the resting cells in the presence of 2 mM potassium cyanide.
Properties of MA32:

| | |
|---|---|
| Cell form | Rods |
| Width | 0.6-0.8 μm |
| Length | 1.5-3.0 μm |
| Motility | + |
| Flagella | polar > 1 |
| Gram reaction | − |
| Lysis by 3% KOH | + |
| Aminopeptidase (Cerny) | + |
| Oxidase | + |
| Catalase | + |
| Growth at 41° C. | − |
| Substrate utilization | |
| Adipate | − |
| Citrate | + |
| Malate | + |
| Phenylacetate | − |
| D-Glucose | + |
| Maltose | − |
| Mannitol | + |
| Arabinose | + |
| Mannose | + |
| Trehalose | + |
| Sorbitol | + |
| Erythrol | + |
| Citraconate | + |

|   |   |
|---|---|
| Inositol | + |
| ADH | + |
| Urease | − |
| Hydrolysis of gelatin | + |
| Hydrolysis of esculin | + |
| Levan from sucrose | + |
| Denitrification | + |
| Lecithinase | + |
| Fluorescence | + |
| Pyocyanin | − |

The profile of the cellular fatty acids is typical of Group I *Pseudomonas*

Analysis of a 484 bp-long segment of the 16S rRNA revealed a 100% agreement with the sequence of *Pseudomonas marginalis*

It was possible, taking account of all the data, to identify MA32 as *Pseudomonas marginalis*.

Properties of MA113:

|   |   |
|---|---|
| Cell form | Rods |
| Width | 0.6-0.8 μm |
| Length | 1.5-3.0 μm |
| Motility | + |
| Flagella | polar > 1 |
| Gram reaction | − |
| Lysis by 3% KOH | + |
| Aminopeptidase (Cerny) | + |
| Oxidase | + |
| Catalase | + |
| Growth at 41° C. | − |
| Substrate utilization |   |
| Adipate | − |
| Citrate | + |
| Malate | + |
| Phenylacetate | + |
| D-Glucose | + |
| Maltose | − |
| Mannitol | − |
| Arabinose | − |
| Mannose | − |
| Trehalose | − |
| Inositol | − |
| β-Alanine | + |
| α-Ketoglutarate | + |
| Benzylamine | + |
| Hippurate | + |
| Azelate | + |
| D-mandelate | + |
| ADH | + |
| Urease | − |
| Hydrolysis of gelatin | − |
| Hydrolysis of esculin | − |
| Levan from sucrose | − |
| Denitrification | − |
| Lecithinase | − |
| Fluorescence | + |
| Pyocyanin | − |

The profile of the cellular fatty acids is typical of Group I *Pseudomonas*

Analysis of a 476 bp-long segment of the 16S rRNA revealed a 100% agreement with the sequence of *Pseudomonas putida*

It was possible, taking account of all the data, to identify MA113 as *Pseudomonas putida*.

Example 3

Determination of the Enzymatic Activity

The cells were grown as described in Example 1, removed from the culture medium by centrifugation and resuspended in standard buffer (50 mM potassium phosphate buffer of pH 7.5). 50 μl of this cell suspension were added to 700 μl of the standard buffer, and the reaction was started by adding 250 μl of a 200 mM solution of the nitrile in standard buffer. The concentration of the cells in the cell suspension was in this case such that the nitrile was 5-30% converted after 10 min at 20° C. After 10 min at 20° C., the reaction was stopped by adding 20 μl of 50% concentrated phosphoric acid, and the cells were removed by centrifugation.

| HPLC analysis |   |
|---|---|
| Column | Intersil ODS-3V (GL Sciences Inc.) |
| Mobile phase | Mixture of 10 mM potassium phosphate buffer of pH 2.3 and acetonitrile in the ratio 85:15 for methionine nitrile, MHA nitrile and acetone cyanohydrin, and 99:1 for all other substrates |
| Flow rate | 1 ml/min |
| Detection | UV at 200 nm |

The activity of one U is defined as the amount of enzyme which converts 1 μmol of methacrylonitrile to the amide in one minute. If the acid was also produced in addition to the amide, one U was defined as the amount of enzyme which converts 1 μmol of methacrylonitrile into the amide and acid in one minute.

Figure 1:
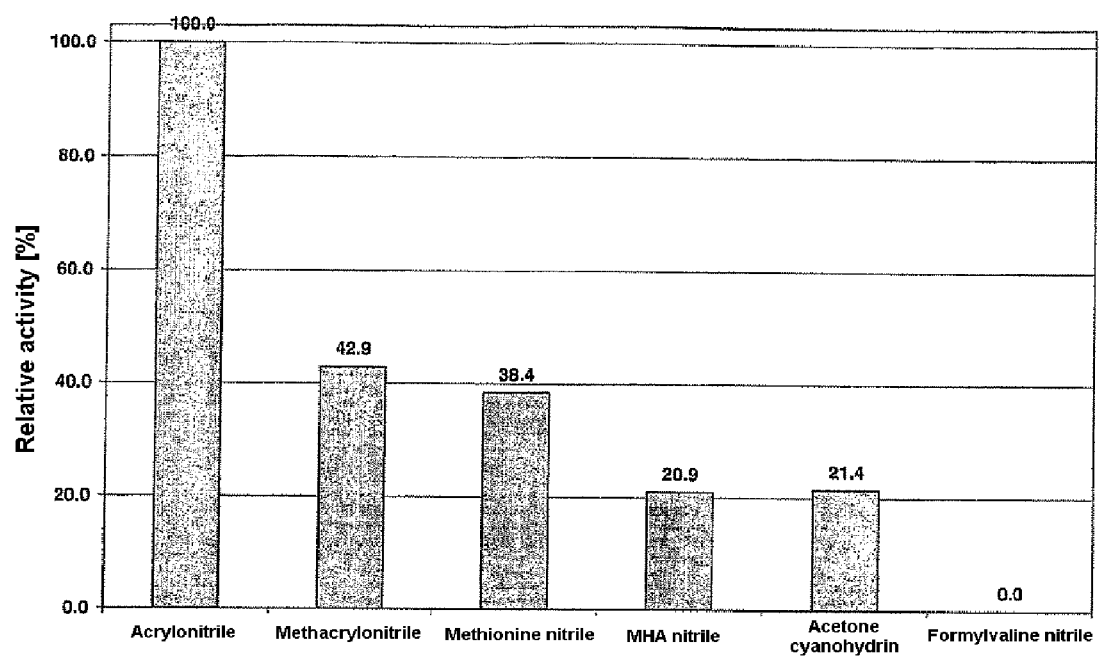
FIG. 1 is a graph showing the relative activity of strain MA32.
Figure 2:
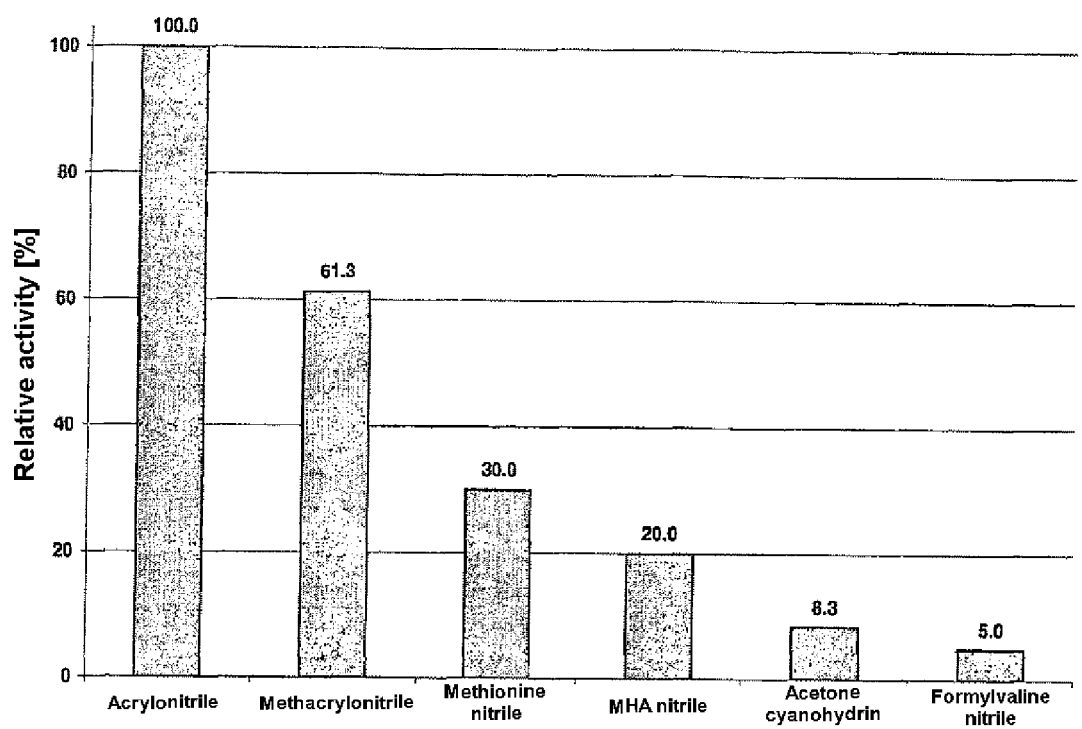
FIG. 2 is a graph showing the relative activity of strain MA113.

The relative activities of the strains MA32 and MA113 are depicted in FIG. 1 and in FIG. 2.

Example 4

Influence of Cyanide on the Activity of the Nitrile Hydratase

50 μl of a cell suspension prepared in analogy to Example 3 were added to 700 μl of the standard buffer which comprised 0, 21.4, 53.6 and 107.1 mM potassium cyanide (final concentration 0, 20, 50, 100 mM cyanide). The reaction was started by adding 200 μl of a 200 mM solution of the nitrile in standard buffer which in each case had the same cyanide concentration as the remaining reaction solution. The concentration of the cells in the cell suspension was in this case such that the nitrile was 16% converted in the mixture without cyanide after 10 min at 20° C. After 10 min at 20° C., the reaction was stopped by adding 20 μl of 50% concentrated phosphoric acid, and the conversion was determined in analogy to Example 2.

Figure 3:
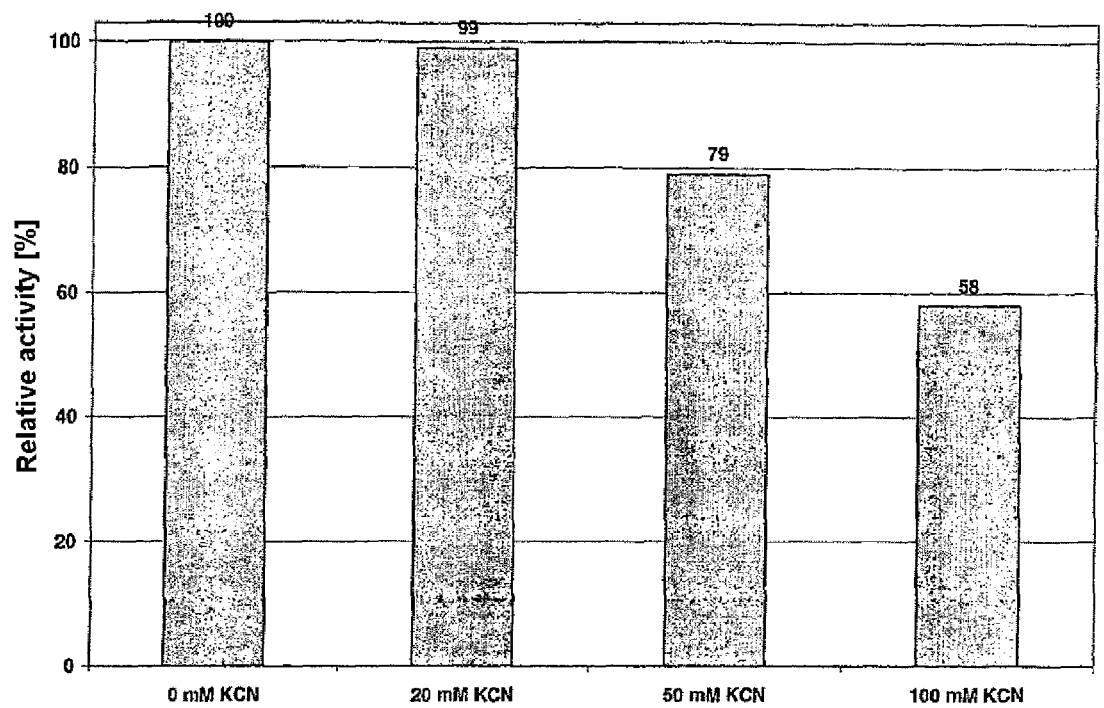
FIG. 3 is a graph showing the relative activities for the conversion of methacrylonitrile as a function of the cyanide concentration of strain MA32.
Figure 4:
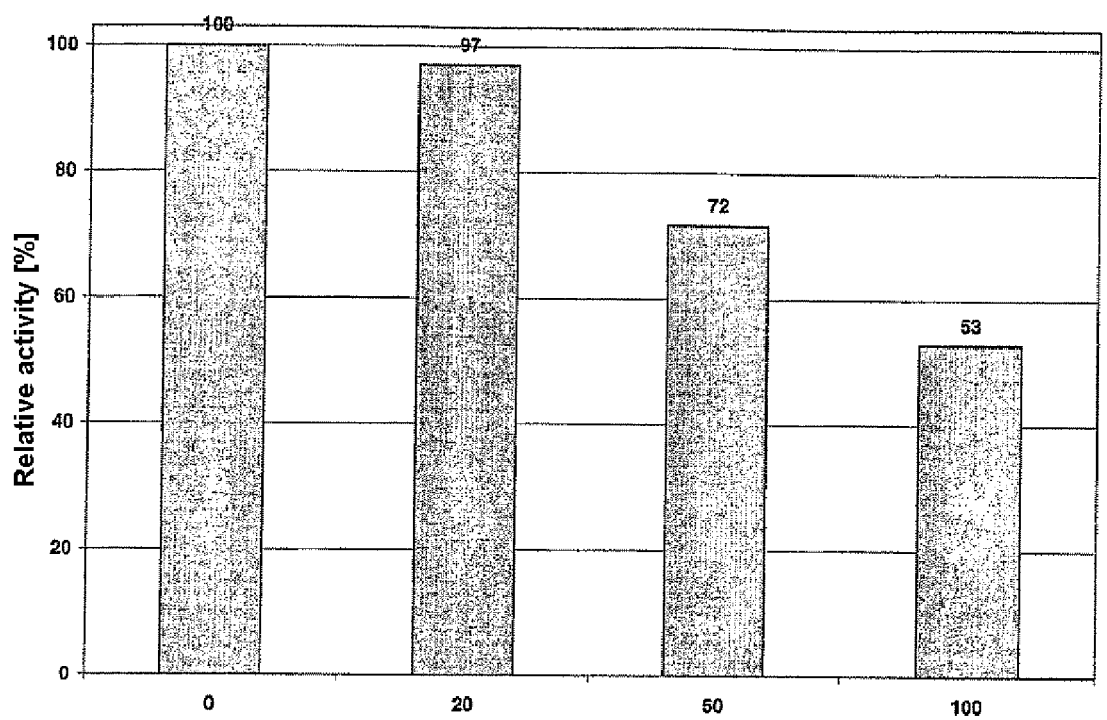
FIG. 4 is a graph showing the relative activities for the conversion of methacrylonitrile as a function of the cyanide concentration of strain MA113.

The relative activities for the conversion of methacrylonitrile as a function of the cyanide concentration are shown in FIG. 3 and in FIG. 4.

Example 5

Conversion of Acetone Cyanohydrin with Resting Cells of *Pseudomonas marginalis* MA32

*Pseudomonas marginalis* MA32 cells were grown and centrifuged as described in Example 1. An amount of the cells which comprised 1.16 g of dry biomass was diluted with 50 mM potassium phosphate buffer of pH 8.0 to a final volume of 50 ml. In addition, 0.02 mM of 2-methyl-1-propaneboronic acid was added to the reaction mixture. Freshly distilled acetone cyanohydrin was added continuously at 4° C. with vigorous stirring at such a rate that the concentration did not exceed 5 g/l at any point during the reaction. The pH was kept constant at 7.5. The reaction was followed by HPLC as described in Example 3. After 140 min, 10.0 g of the nitrile had been completely converted into 10.7 g of amide and 1.4 g of acid.

Figure 5:
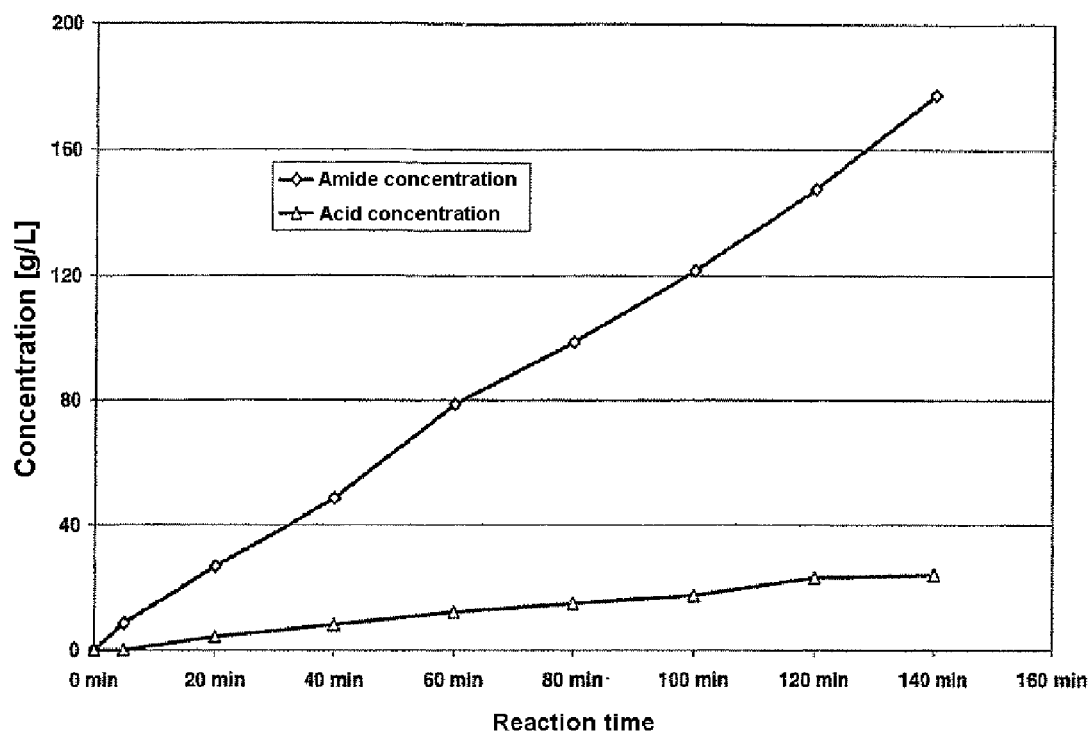
FIG. 5 shows the time course of conversion of acetone cyanohydrin achieved with strain MA113.

The time course of the reaction achieved with the strain MA113 is depicted in FIG. 5.

Example 6

Conversion of Crude MHA Nitrile with Resting Cells of *Pseudomonas marginalis* MA32

*Pseudomonas marginalis* MA32 cells were grown and centrifuged as described in Example 1. An amount of the cells which comprised 0.34 g of dry biomass was diluted with 50 mM potassium phosphate buffer of pH 8.0 to a final volume of 70 ml. In addition, 0.02 mM 2-methyl-1-propaneboronic acid was added to the reaction mixture. The crude MHA nitrile was added continuously at 4° C. with vigorous stirring at such a rate that the concentration did not exceed 10 g/l at any point during the reaction. The pH was kept constant at 8.0. The reaction was followed by HPLC as described in Example 3. After 510 min, 10.05 g of The nitrile had been completely converted into 11.13 g of amide and 0.31 g of acid. This corresponds to a final concentration of 139 g of amide per liter.

The MHA nitrile had been prepared directly from 3-methylthiopropionaldehyde and a slight excess of hydrocyanic acid. A 50 mM solution of this MHA nitrile in water contained 0.5 mM cyanide (Spektroquant', Merck).

Figure 6:
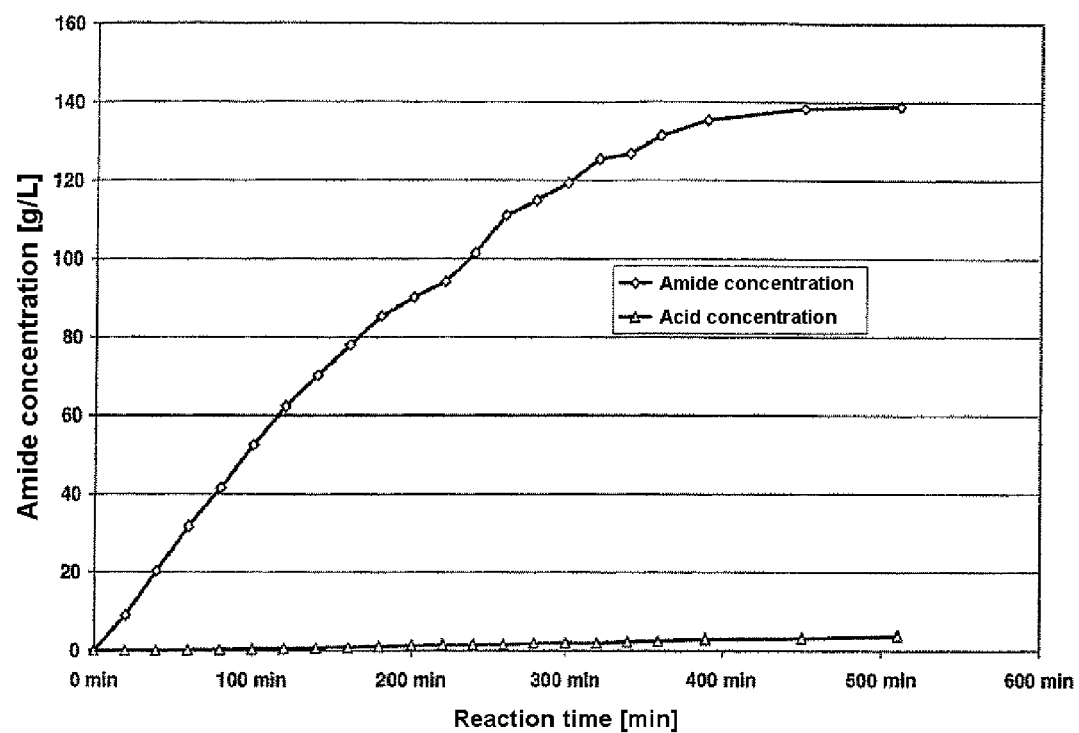
FIG. 6 shows the time course of conversion of crude MHA nitrile achieved with strain MA32.

The time course of the reaction achieved with the strain MA32 is depicted in FIG. 6.

Example 7

Cloning of the Nitrile Hydratase Gene Cluster from *Pseudomonas marginalis* MA 32 and Construction of an Expression Vector The gene cluster of the nitrile hydratase comprising an α subunit, β subunit and a nitrile hydratase activator protein whose coexpression is essential for the activity of the nitrile hydratase (Nojiri et al., 1999, Journal of Biochemistry, 125: 696-704) was amplified by PCR using the primers 1F and 1R which introduced cleavage sites for the restriction enzymes NdeI and HindIII. The PCR product obtained in this way was ligated into a vector cut with NdeI and HindIII, with the introduced genes being under the control of the rhamnose promoter. The expression vector produced in this way is called pKE31.

The restriction map is to be found in FIG. 7 and the sequence in SEQ ID NO:1.

The expression plasmid was transformed into the strain *E. coli* DSM 14459 which had been deposited at the Deutsche Sammiung von Mikroorganismen und Zellkulturen GmbH (DSMZ) on Aug. 22, 2001.

Primers:

```
1F 5'-CTC CAC CAT ATG AGT ACA GCT ACT TCA ACG-3'

1R 5'-CTT CAT AAG CTT CTA TCT CGG ATC AAA TGG-3'

1F: SEQ ID NO: 11

1R: SEQ ID NO: 12
```

The genes are located on the following segments of SEQ ID NO: 1:

| Gene of the α subunit: | nt | 25-609 |
|---|---|---|
| Gene of the β subunit: | nt | 650-1312 |
| Gene of the activator protein: | nt | 1309-2577 |

Example 8

Cloning of the Nitrile Hydratase Gene Cluster from *Pseudomonas putida* MA113

The gene cluster of the nitrile hydratase consisting of α subunit, β subunit and a nitrile hydratase activator protein whose coexpression is essential for the activity of the nitrile hydratase (Nojiri et al., 1999, Journal of Biochemistry, 125: 696-704) was amplified by PCR using the primers 1F and 1R.

The sequence is to be found in SEQ ID NO: 6.

Primers:

```
2F 5'-ATG ACG GCA ACT TCA ACC CCT GGT G-3'

2R 5'-TCA GCT CCT GTC GGC AGT CG-3'

2F: SEQ ID NO: 13

2R: SEQ ID NO: 14
```

The genes are located on the following segments of SEQ ID NO: 5:

| Gene of the α subunit: | nt | 1-582 |
|---|---|---|
| Gene of the β subunit: | nt | 624-1286 |
| Gene of the activator protein: | nt | 1283-2360 |

Example 9

Heterologous Expression of the Nitrile Hydratases from *Pseudomonas marginalis* MA 32 in *E. coli* DSM 14459

*E. coli* DSM 14459 was deposited in connection with DE 101 55 928.

The cells transformed with pKE31 were grown in LB medium (LB broth, Miller, VWR) which contained 2 mM iron(III) citrate and 100 μg/ml ampicillin at 37° C. with shaking. After 12-16 hours, an amount of the preculture was transferred into a main culture such that the latter had an OD600 of 0.1. The culture medium of the main culture corresponded to that of the preculture but additionally contained 2 g/l L-rhamnose. The cells were harvested after cultivation at 30° C. for 22 hours.

Example 10

Determination of the Enzymatic Activities

The culturing of the cells and the determination of the activity were carried out as described in Example 9 and Example 3.

The cells of the strain *E. coli* DSM 14459 transformed with the plasmid pKE31 had a specific activity of 17 U/mg of DBM.

Example 11

Determination of the Enzymatic Activities in the Presence of 100 mM Potassium Cyanide The culturing of the cells and the determination of the activities in the presence of 100 mM potassium cyanide were carried out as described in Example 9 and Example 4.

The cells of the strain *E. coli* DSM 14459 transformed with the plasmid pKE31 had a specific activity of 11 U/mg of DBM.

What is claimed is:

1. An isolated polynucleotide selected from the group consisting of:
    a) polynucleotides having SEQ ID NO:1, SEQ ID NO:4, or the complement thereof,
    b) polynucleotides which encode a polypeptide having SEQ ID NO:2, SEQ ID NO:3, or SEQ ID NO:5,
    c) polynucleotides which hybridize with the complementary sequences of the polynucleotides of a) or b) under stringent conditions, where stringent conditions mean washing in 5×SSC at a temperature of from 50 to 65° C.

2. An isolated polypeptide encoded by the polynucleotide of claim 1.

3. A vector comprising the polynucleotide of claim 1.

4. A host cell transformed or transfected by the introduction of the polynucleotide of claim 1 or a vector comprising the polynucleotide.

5. A host cell transformed by the introduction of a vector as claimed in claim 3.

6. A recombinant microorganism of the genus Pseudomonas deposited under the number DSM 16275 or DSM 16276.

* * * * *